United States Patent
Bhan et al.

(10) Patent No.: US 7,858,309 B2
(45) Date of Patent: Dec. 28, 2010

(54) METHOD FOR DIFFERENTIATING BETWEEN MULTIPLE SCLEROSIS SUBTYPES

(75) Inventors: Virender Bhan, Halifax (CA); John W. Gillard, Baie D'Urfé (CA); Andrea Hebb, Eastern Passage (CA); Martin Holcik, Ottawa (CA); Robert G. Korneluk, Ottawa (CA); George Robertson, Halifax (CA)

(73) Assignee: Dianovix, Inc., Halifax, Nova Scotia (CA)

( * ) Notice: Subject to any disclaimer, the term of this patent is extended or adjusted under 35 U.S.C. 154(b) by 576 days.

(21) Appl. No.: 11/702,657

(22) Filed: Feb. 6, 2007

(65) Prior Publication Data

US 2008/0020388 A1    Jan. 24, 2008

Related U.S. Application Data

(60) Provisional application No. 60/765,734, filed on Feb. 7, 2006.

(51) Int. Cl.
- *C12Q 1/68* (2006.01)
- *C12P 19/34* (2006.01)
- *C07H 21/02* (2006.01)
- *C07H 21/04* (2006.01)

(52) U.S. Cl. .................. 435/6; 435/91.2; 536/23.1; 536/24.3

(58) Field of Classification Search ........................ None
See application file for complete search history.

(56) References Cited

PUBLICATIONS

Hebb, A. et al., "Apoptosis-related genes as markers of disease subtypes and treatment response in multiple sclerosis", Can. J. Neurol. Sci., Suppl. 1, pp. S55-S56 (2005).*

Sharief, M.K. et al., Upregulation of the inhibitor of apoptosis proteins in activated T lymphocytes from patients with multiple sclerosis, Journal of Neuroimmunology, 199 (2001), 350-357.

Semra, Y.K. et al, Disease activity in multiple sclerosis correlates with T lymphocyte expression of the inhibitor of apoptosis proteins, Journal of Neuroimmunology, 122 (2002), 159-166.

Chawla-Sarkar, Mamta et al., Preferential Induction of apoptosis by interferon (IFN)-β compared with IFN-α2 : Correlation with TRAIL/Apo2L Induction in melanoma cell lines, Clinical Cancer Research, vol. 7, 1821-1831, Jun. 2001.

Leaman, Douglas W. et al., Identification of X-linked inhibitor of apoptosis-associated Factor-1 as an Interferon-stimulated gene that augments TRAIL Apo2L-induced apoptosis, The Journal of Biological Chemistry, vol. 277, No. 32, Aug. 9, 2002, 28504-28511.

Sharief, M.K. et al., Reduced expression of the inhibitor of apoptosis proteins in T cells from patients with multiple sclerosis following interferon-β therapy, Journal of neuroimmunology 129, (2002), 224-231.

Sharief, M.K. et al., Upregulated survivin expression in activated T lymphocytes correlates with disease activity in multiple sclerosis, European Journal of Neurology, 2002, 9, 503-510.

* cited by examiner

*Primary Examiner*—Teresa E Strzelecka
(74) *Attorney, Agent, or Firm*—Philip Swain; Fasken Martineau DuMoulin LLP

(57) ABSTRACT

Disclosed herein is a method for differentiating between multiple sclerosis subtypes in a patient. The method comprises a) determining an amount of an IAP gene expression level in a blood sample obtained from the patient; and b) correlating the amount of the IAP gene expression level in the blood sample with the presence of a multiple sclerosis subtype in the patient.

10 Claims, 7 Drawing Sheets

METHOD FOR DIFFERENTIATING BETWEEN MULTIPLE SCLEROSIS SUBTYPES

CROSS REFERENCE TO RELATED APPLICATIONS

Applicants hereby claim priority from previously filed U.S. Provisional Patent Application Ser. No. 60/765,734, filed Feb. 7, 2006, the entire contents of which are hereby incorporated by reference.

FIELD OF THE INVENTION

The present invention concerns methods for differentiating between multiple sclerosis subtypes, and more particularly to methods of using different IAP expression levels as markers for the multiple sclerosis subtypes.

BACKGROUND OF THE INVENTION

Multiple sclerosis (MS) is a progressive neurological disorder characterized by an autoimmune mediated attack against the myelin sheath in the CNS resulting in inflammation, demyelination, gliosis and ultimately axonal degeneration [Bruck and Stadelmann 2003]. The clinical course of MS has been divided into four major categories: RR, SP, PP and benign. Patients who have clinical relapses every few months or years with intervening periods of clinical stability define RRMS. RRMS is twice as common in females than males in the second or third decade of life [Noseworthy et al. 2000]. Although the majority of MS patients are initially diagnosed with RRMS, over time increasing numbers of these individuals convert to SPMS characterized by a gradual decline in neurological function [Trojano et al. 2003]. Approximately 15% of MS patients have PPMS characterized by an absence of clinical relapses and an unrelenting deterioration of neurological function from disease onset [McDonnell and Hawkins 2002]. PPMS is characterized by relatively late-onset (mean age ~39 years) although it has been suggested based on clinical and MRI data that the pre-clinical phase of PPMS occurs during the same time frame as in RRMS. In PPMS as in RRMS the CNS lesions have the same age of onset, but it takes 10 years for PPMS patients to develop symptoms [McDonnell et al. 2003]. MRI with the contrast agent gadolinium is often employed during or following an initial attack to identify lesions within the CNS that are consistent with a diagnosis of MS. MRI is also used at protracted intervals in MS patients to identify new areas of demyelinated plaques within the brain and spinal cord [Calabresi 2004]. Moreover, MRI activity correlates with immune cell perturbations in early possible MS. For example, Rinaldi et al. (2006) demonstrated that distinct changes in peripheral lymphocyte subsets occur over the course of 1 year, which differentiate MRI active, and MRI inactive patients following a clinically isolated syndrome. Yet results obtained by MRI do not correlate with clinical disability and are therefore not recommended as therapeutic end-points for new MS therapeutics [Siva 2006]. In addition to RRMS, SPMS and PPMS, there is a benign form of the disease that affects approximately 15% of RRMS patients. Benign MS is arbitrarily defined in RRMS patients who after more than 10 to 15 years following initial diagnosis are still mobile and show only mild deficits (EDSS≦4). Typically, these patients show little or no progression after their initial attack. Moreover, those patients with an EDSS score of ≦2 and disease duration of more than 10 to 15 years tend to maintain a low EDSS disability score for an additional 10 years. Benign MS requires no therapeutic intervention, however, it is not possible to diagnose this form of MS until at least 5 to 10 years from MS onset [Hawkins and McDonnell 1999; Pittock et al. 2004]. Unfortunately, there are no diagnostic tests that would allow a clinician to predict whether a newly diagnosed MS patient will follow a benign or aggressive disease course.

MS is considered to be a T cell-mediated autoimmune disease of the brain and spinal cord [Traugott et al. 1983; Vizler et al. 1999]. While there appears to be a localized CNS immune response, peripheral immune cell abnormalities appear to correlate with central disease activity [Hafler and Weiner 1989] and may precede MRI activity. Apoptosis is an important mechanism in immune system regulation, responsible for elimination of autoreactive T-lymphocytes (T cells), B-lymphocytes (B cells) and monocytes from the circulation and prevention of their entry into the CNS [Mahoney and Rosen 2005; Todaro et al. 2004]. It has been hypothesized that a genetic predisposition exists in MS patients whereby a failure of autoreactive T cells and B cells as well as activated macrophages to undergo apoptosis contributes to the pathogenesis of MS [Bernard and Derosbo 1992; Pender 1998; Pender and Rist 2001]. Consistent with this hypothesis expression of members of the IAP family of anti-apoptotic proteins are elevated in mitogen (PHA) stimulated T cells derived from the CSF or blood of MS patients relative to healthy or neurological control subjects [Segal and Cross 2000; Seki et al. 1988; Semra et al. 2002; Sharief et al. 2002b; Sharief and Semra 2001; Tsukamoto et al. 1986]. The IAP family of anti-apoptotic genes encodes proteins that directly bind to and inactivate initiator and effector caspases, a group of cysteinyl proteases that mediate the initiation and execution of apoptosis [Holcik et al. 2001; Salvesen and Duckett 2002]. First discovered in baculovirus, the IAPs are well conserved in eukaryotes, ranging from yeast to humans and to date, eight human IAPs have been identified [Holcik et al. 2001; Nachmias et al. 2004]. Importantly, IAPs are the only intrinsic inhibitors of caspases. The IAPs are typified by the presence of a variable number of highly conserved domains about 70 amino acids in length, known as BIR domains, which are critical for anti-apoptotic activity. For example, while XIAP, HIAP-1 and HIAP-2 contain three BIR domains, survivin possesses only one BIR domain. Although highly similar, the individual BIR domains are not functionally equivalent. The BIR2 domain and the preceding linker region of XIAP, HIAP-1, and HIAP-2 facilitate the interaction with and suppression of caspases 3 and 7; the two most potent effector caspases [Eckelman and Salvesen 2006; Nachmias et al. 2004; Robertson et al. 2000]. Inhibition of the initiatior caspase 9 is accomplished by the BIR3 domain. While XIAP, HIAP-1 and HIAP-2 possess BIR domains 2 and 3 capable of binding caspases 7 and 9, only XIAP contains critical domain residues capable of direct caspase inhibition [Eckelman and Salvesen 2006]. In addition to BIR domains, XIAP, HIAP-1 and HIAP-2 possess a carboxy-terminal RING zinc finger motif that has E3 ubiquitin ligase activity targeting caspases for degradation by proteosomes [Holcik et al. 2001]. In addition, it has been shown recently that IAPs are themselves controlled by ubiquitin-mediated degradation. For example, HIAP-1 is a direct target for HIAP-2-mediated ubiquitination and proteosomal degradation [Conze et al. 2005]. The RING domain of XIAP also mediates polyubiquitination of TAK-1, an enzyme responsible for activation of the pro-apoptotic kinase, JNK [Kaur et al. 2005]. In this fashion, XIAP is able to target TAK-1 for degradation by the proteosome thereby preventing JNK-mediated apoptosis. Structurally similar, both HIAP-1 and HIAP-2 possess a CARD, a highly conserved domain noted to promote homodimerization and oligomerization with other CARD containing proteins. While elevated expression of XIAP, HIAP-1, HIAP-2 and survivin in mitogen-stimulated T cells from patients with active RRMS correlates with clinical features of disease activity, deficits in Fas mediated cell death [Comi et al. 2000] and T cell resistance to apoptosis [Sharief et al. 2002b; Sharief and Semra 2001], a systematic examination of the expression patterns of these genes in whole blood, PBMN and resting T cells in patients with various forms of MS has yet to be done. Given that the failed apoptosis of auto-reactive T cells has been implicated in MS pathogenesis and that MS is a clinically heterogeneous disorder [Chofflon 2005], it would be advantageous if specific patterns of IAP expression in different immune cell subtypes could be measured and correlated with distinct forms of the disease. Furthermore, it would be highly advantageous to develop a reliable, rapid and inexpensive diagnostic test for multiple sclerosis subtypes based on specific patterns of basal IAP gene expression in peripheral immune cells. Finally, a diagnostic test would allow clinicians to decide whether interferon drug treatment is appropriate for a specific disease subtype.

SUMMARY OF THE INVENTION

We have unexpectedly discovered that human patients suffering from the major categories (or subtypes) of multiple sclerosis (MS) have basal IAP gene expression profiles that correlate with the disease severity. Specifically, we have discovered that XIAP and HIAP-2 are differentially expressed in high levels and are associated with aggressive forms of the disease including active relapsing remitting MS and secondary progressive MS. Advantageously, the gene expression profiles of XIAP and HIAP-2 are useful as diagnostic markers that may aid early diagnosis of the aggressive forms of MS. Furthermore, the unique IAP gene expression profiles allow differentiation between the various subtypes of MS. With early diagnosis, patients can be treated more rapidly than previously allowable thereby ensuring optimal therapeutic response. Moreover, the differences in IAP expression profiles are predictive of interferon-β (IFN-β) responsiveness, which will allow clinicians to appropriately select patients for whom the use IFN-β drugs will provide maximum benefit and avoid the use of IFN-β drugs, which are expensive, on patients who suffer from benign and primary progressive MS for which little or no therapeutic benefit will be afforded. Moreover, in patients suffering from PPMS, we have also discovered that survivin expression is elevated in the resting T cells compared to XIAP, HIAP 1 and HIAP-2. Surprisingly, in mRNA extracted from whole blood, NAIP mRNA levels were elevated in all forms of MS except those patients with benign MS or normal subjects.

According to one embodiment of the present invention, there is provided a method for differentiating between multiple sclerosis subtypes in a patient, the method comprising:
  a) determining an amount of an IAP gene expression level in a blood sample obtained from the patient; and
  b) correlating the amount of the IAP gene expression level in the blood sample with the presence of a multiple sclerosis subtype in the patient.

In one aspect, typically the IAP gene expression level is compared those of control subjects. An increase in the IAP gene expression level relative to those of the control subjects indicates that the patient is suffering from the MS subtype. The control subjects are those having benign MS or are healthy normal subjects. The MS subtype is benign MS, quiescent relapsing remitting MS, active relapsing remitting MS, primary progressive MS or secondary progressive MS. The IAP gene expression level is determined by measuring the levels of transcribed IAP mRNA in the blood sample. The level of IAP mRNA is measured using quantitative real time polymerase chain reaction (qRT-PCR).

In one aspect of the present invention, the IAP gene expression level is determined by measuring the level of IAP protein in the blood sample. The IAP protein level is measured using an immunoassay.

In another aspect, the IAP gene encodes an IAP protein selected from NAIP, XIAP, HIAP-1, HIAP-2 or survivin.

In another aspect, typically peripheral blood mononuclear (PBMN) cells are isolated from the blood sample. The IAP gene expression level is measured in the PBMNs. The IAP gene expression level is compared to those of control subjects, an increase in the IAP gene expression level relative to those of the control subjects indicates that the patient is suffering from the MS subtype. The increased gene expression level includes increased levels of XIAP mRNA and HIAP-2 mRNA. The MS subtype is active relapsing remitting MS. The MS subtype is secondary progressive MS. Typically, the control subjects are those having benign MS, or are healthy normal subjects.

In another aspect, typically T cells are isolated from the blood sample. The IAP gene expression level is measured in the T cells. The T cells are resting T cells.

In one aspect, typically, the IAP gene expression level is compared to those of control subjects, an increase in the IAP gene expression level relative to those of the control subjects indicates that the patient is suffering from the MS subtype. The increased gene expression level includes increased levels of HIAP-1 mRNA or HIAP-2 mRNA. The increased levels of only HIAP-1 mRNA indicate that the patient is suffering from quiescent relapsing remitting MS. The increased levels of HIAP-1 mRNA and HIAP-2 mRNA levels indicate that the patient is suffering from active relapsing remitting MS. The increased levels of only HIAP-2 mRNA indicate that the patient is suffering from secondary progressive MS. The increased gene expression level includes increased levels of survivin mRNA. The increased level of survivin mRNA indicates that the patient is suffering from primary progressive MS. The control subjects are those having benign MS, or are healthy normal subjects. The level of HIAP-2 expression correlates to the degree of disability measured by EDSS scores.

In another aspect, the blood sample is whole blood. The IAP gene expression is measured in the whole blood. The IAP gene expression level is compared to those of control subjects, an increase in the IAP gene expression level relative to those of the control subjects indicates that the patient is suffering from the MS subtype. The increased gene expression level includes increased levels of NAIP mRNA in patients who are suffering from relapsing remitting MS, quiescent relapsing remitting MS, primary progressive MS and secondary progressive MS. The control subjects are those having benign MS or are healthy normal subjects.

According to another embodiment of the present invention, there is provided a method for differentiating active relapsing remitting multiple sclerosis in a patient, the method comprising:
  a) determining an amount of XIAP and HIAP-2 gene expression levels in peripheral blood mononuclear (PBMN) cells obtained from the patient; and
  b) comparing the amount of the XIAP and HIAP-2 gene expression levels in the PBMNs with the XIAP and HIAP-2 gene expression levels of control subjects, an increase in the XIAP and HIAP-2 gene expression levels being an indication that the patient is suffering from active relapsing remitting multiple sclerosis.

According to another embodiment of the present invention, there is provided a method for differentiating secondary progressive multiple sclerosis in a patient, the method comprising:
  a) determining an amount of XIAP and HIAP-2 gene expression levels in peripheral blood mononuclear (PBMN) cells obtained from the patient; and
  b) comparing the amount of the XIAP and HIAP-2 gene expression levels in the PBMNs with the XIAP and HIAP-2 gene expression levels of control subjects, an increase in the XIAP and HIAP-2 gene expression levels being an indication that the patient is suffering from secondary progressive multiple sclerosis.

According to another embodiment of the present invention, there is provided a method for differentiating quiescent relapsing remitting multiple sclerosis in a patient, the method comprising:
  a) determining an amount of HIAP-1 gene expression level in T cells obtained from the patient; and
  b) comparing the amount of the HIAP-1 gene expression level in the T cells with the HIAP-1 gene expression levels of control subjects, an increase in the HIAP-1 gene expression levels being an indication that the patient is suffering from quiescent relapsing remitting multiple sclerosis.

According to another embodiment of the present invention, there is provided a method for differentiating active relapsing remitting multiple sclerosis in a patient, the method comprising:
  a) determining an amount of HIAP-1 and HIAP-2 gene expression levels in T cells obtained from the patient; and
  b) comparing the amount of the HIAP-1 and HIAP-2 gene expression levels in the T cells with the HIAP-1 and HIAP-2 gene expression levels of control subjects, an increase in the HIAP-1 and HIAP-2 gene expression levels being an indication that the patient is suffering from active relapsing remitting multiple sclerosis.

According to an alternative embodiment of the present invention, there is provided a method for differentiating between quiescent and active relapsing remitting multiple sclerosis in a patient, the method comprising:
  a) determining an amount of HIAP-1 and HIAP-2 gene expression levels in T cells obtained from the patient; and
  b) comparing the amount of the HIAP-1 and HIAP-2 gene expression levels in the T cells with the HIAP-1 and HIAP-2 gene expression levels of control subjects, either an increase in only HIAP-1 gene expression levels being an indication that the patient is suffering from quiescent relapsing remitting multiple sclerosis, or an increase in both the HIAP-1 and HIAP-2 gene expression levels being an indication that the patient is suffering from active relapsing remitting multiple sclerosis.

According to another alternative embodiment of the present invention, there is provided a method for differentiating secondary progressive multiple sclerosis in a patient, the method comprising:
  a) determining an amount of HIAP-2 gene expression level in T cells obtained from the patient; and
  b) comparing the amount of the HIAP-2 gene expression level in the T cells with the HIAP-2 gene expression levels of control subjects, an increase in the HIAP-2 gene expression levels being an indication that the patient is suffering from secondary progressive multiple sclerosis.

According to another embodiment of the present invention, there is provided a method for differentiating primary progressive multiple sclerosis in a patient, the method comprising:
  a) determining an amount of survivin gene expression level in T cells obtained from the patient; and
  b) comparing the amount of the survivin gene expression level in the T cells with the survivin gene expression levels of control subjects, an increase in the survivin gene expression levels being an indication that the patient is suffering from primary progressive multiple sclerosis.

According to another embodiment of the present invention, there is provided a method for differentiating between benign and either relapsing remitting MS, primary progressive MS or secondary progressive MS in a patient, the method comprising:
  a) determining an amount of NAIP gene expression levels in whole blood obtained from the patient; and
  b) comparing the amount of NAIP gene expression levels with the amount of NAIP gene expression levels in control subjects, an increase in the NAIP gene expression levels being an indication that the patient is suffering from either relapsing remitting MS, primary progressive MS or secondary progressive MS and not benign MS.

According to another embodiment of the present invention, there is provided a method of testing a patient's suitability for interferon-β treatment of multiple sclerosis, the method comprising:
  a) determining an amount of an IAP gene expression level in a blood sample obtained from the patient suspected of having an aggressive subtype of multiple sclerosis; and
  b) comparing the amount of the IAP gene expression level to the IAP gene expression levels of control subjects, an increase in IAP gene expression levels being an indication that the patient is suffering from an aggressive subtype of multiple sclerosis, the patient being suitable for treatment with interferon-β.

According to another embodiment of the present invention, there is provided a method of identifying whether a patient is at risk of developing secondary progressive multiple sclerosis from active relapsing remitting multiple sclerosis, the method comprising:
  a) obtaining a blood sample for the patient; and
  b) comparing XIAP mRNA levels in PBMNs isolated from the sample, and HIAP-1 and HIAP-2 mRNA levels in T cells isolated from the sample, with those of a control subject, an increase in the XIAP mRNA levels in the PBMNs and an increase the HIAP-2 mRNA levels in the T cells, and normal HIAP-1 levels in the T cells, being an indication that the patient is at risk of developing secondary progressive MS. The method further including detecting a normalization of HIAP-1 in T cells.

According to an alternative embodiment of the present invention, there is provided use of IAP mRNA expression or IAP protein expression as a biomarker for the differentiation of multiple sclerosis subtypes in a subject, an increased level of expression compared to control subjects being an indication that the patient has a multiple sclerosis subtype.

According to another embodiment of the present invention, there is provided a method for monitoring the progress of a multiple sclerosis therapy of a patient, the method comprising:

a) determining an amount of an IAP gene expression level in a first blood sample obtained from the patient at first time period;
b) determining an amount of the IAP gene expression level in a second blood sample obtained from the patient at a second time period; and
b) comparing in the IAP gene expression levels, a decrease in the IAP gene expression level at the second time period being an indication that the patient is responding to the multiple sclerosis therapy.

According to an alternative embodiment of the present invention, there is provided a diagnostic kit for differentiating a patient suspected of having a subtype of multiple sclerosis, the kit comprising:
a) a vessel or vessels for receiving a blood sample from the subject;
b) an agent that specifically detects IAP protein or amplifies IAP mRNA; and
c) printed instructions for detecting the IAP protein or the amplified IAP mRNA in the sample.

In one aspect, typically, the agent for amplifying the IAP mRNA are the primers and probes selected form Table 2. The IAP protein is detected using immunoassays. The immunoassay is an ELISA.

According to another embodiment of the present invention, there is provided a method of differentiating between multiple sclerosis subtypes in a patient blood sample, the method comprising:
a) determining an amount of an IAP gene expression level in the blood sample; and
b) correlating the amount of the IAP gene expression level in the blood sample with the presence of a multiple sclerosis subtype.

According to an alternative embodiment of the present invention, there is provided a method for the differentiation of a multiple sclerosis subtype in a subject, the method comprising:
a) obtaining a peripheral blood sample from the subject; and
b) detecting an increased level of IAP mRNA in the sample compared to the level in a healthy subject, wherein the increased level of the IAP mRNA is diagnostic of the multiple sclerosis subtype in the subject.

Examples of IAPs that are useful in practicing the methods of the invention include, but are not limited to, human and mouse survivin, NAIP, XIAP, HIAP-1 (cIAP2), and HIAP-2 (cIAP1), which are disclosed U.S. Pat. Nos. 5,919,912; 6,156,535; 6,656,704; 6,020,127; 6,656,684; 6,429,011; 6,994,957; US2002/0137028.

BRIEF DESCRIPTION OF THE DRAWINGS

Further aspects and advantages of the present invention will become better understood with reference to the description in association with the following Figures, wherein.

DETAILED DESCRIPTION OF THE INVENTION

Definitions

Figure 1:
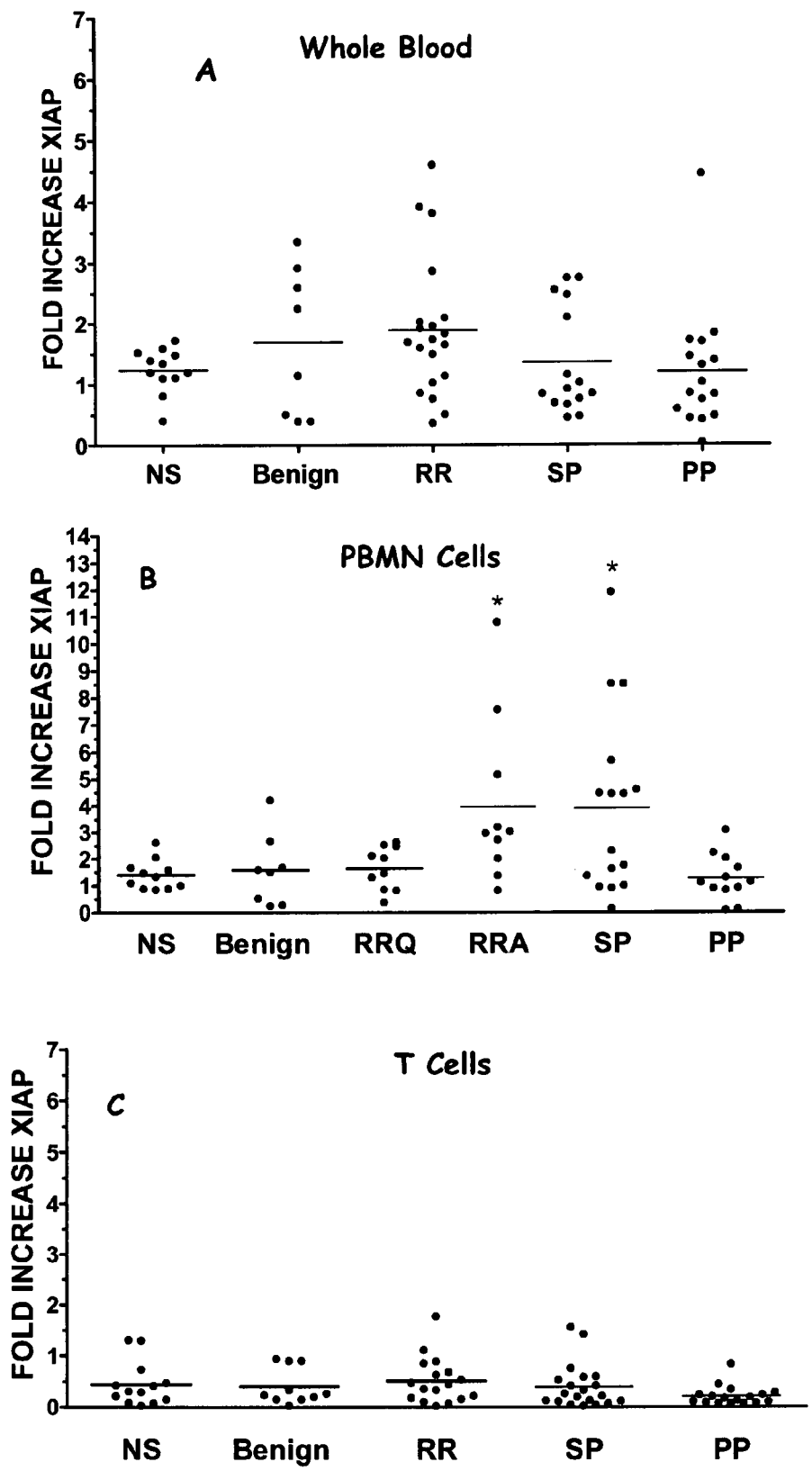
FIGS. 1A to 1C are graphs illustrating the relative quantification of XIAP mRNA expression in RNA extracted from (A) whole blood, (B) PBMN cells and (C) T cells employing qRT-PCR. The graphs depict the expression of XIAP mRNA relative to the expression of the endogenous control gene $\beta_2$ microglobulin ($2^{-\Delta\Delta CT}$) in normal subjects (NS) and patients with benign, Relapsing-Remitting (RR), Secondary-Progressive (SP) or Primary-Progressive (PP) MS patients. Quiescent (Q)=MS symptoms in remission at time of blood draw and the patient has not experienced any relapses in the 2 years prior to blood draw; Active (A)=MS symptoms are active at time of blood draw and the patient has experienced at least one relapse in the 2 years prior to blood draw. (A) XIAP gene expression in whole blood was not affected in MS relative to NS. (B) XIAP gene expression is increased in PBMN cell RNA of RRA and SPMS patients relative to NS. Note also that XIAP mRNA levels are higher in patients whose symptoms are active (RRA) rather than quiescent (RRQ). (C) XIAP gene expression in T cells is similar among NS and all subtypes of MS patients. *p<0.05.

Unless otherwise stated, the following terms apply:

The singular forms "a", "an" and "the" include corresponding plural references unless the context clearly dictates otherwise.

As used herein, the term "comprising" is intended to mean that the list of elements following the word "comprising" are required or mandatory but that other elements are optional and may or may not be present.

As used herein, the term "consisting of" is intended to mean including and limited to whatever follows the phrase "consisting of". Thus the phrase "consisting of" indicates that the listed elements are required or mandatory and that no other elements may be present.

As used herein the terms "apoptosis" is intended to mean the process of cell death in which a dying cell displays a set of well-characterized biochemical indicia that include cell membrane blebbing, cell soma shrinkage, chromatin condensation, and DNA laddering.

As used herein, the term "cell" is intended to mean a single-cellular organism, a cell from a multi-cellular organism or it may be a cell contained in a multi-cellular organism.

As used herein, the term "subject" or "patient" is intended to mean humans and non-human mammals such as primates, cats, dogs, swine, cattle, sheep, goats, horses, rabbits, rats, mice and the like. In one example, the subject is a human.

As used herein, the term "IAP gene" is intended to mean a gene encoding a polypeptide having at least one BIR domain and which is capable of modulating (inhibiting or enhancing) apoptosis in a cell or tissue. The IAP gene is a gene having about 50% or greater nucleotide sequence identity to at least one of survivin, NAIP, HIAP-1 (cIAP2), HIAP-2 (cIAP1), and XIAP. The region of sequence over which identity is measured is a region encoding at least one BIR domain and a ring zinc finger domain. Mammalian IAP genes include nucleotide sequences isolated from any mammalian source. In one example, the mammal is a human.

As used herein, the term "protein", "polypeptide" or "polypeptide fragment" is intended to mean any chain of more than two amino acids, regardless of post-translational modification, for example, glycosylation or phosphorylation, constituting all or part of a naturally occurring polypeptide or peptide, or constituting a non-naturally occurring polypeptide or peptide.

As used herein, the term "IAP protein" or "IAP polypeptide" is intended to mean a polypeptide or protein, or fragment thereof, encoded by an IAP gene. Examples of IAP polypeptides include, but are not limited to, survivin, NAIP, HIAP-1 (cIAP2), HIAP-2 (cIAP1), and XIAP.

As used herein, the term "blood sample" is intended to mean whole blood taken from the periphery of the subject from which immune cells, for example, peripheral blood mononuclear (PBMN) cells; and T cells can be isolated.

As used herein, the term "IAP mRNA expression" is intended to mean expression of IAP genes which encode survivin, NAIP, XIAP, HIAP-1 and HIAP-2.

As used herein the term "IAP gene expression level" is intended to mean a measurable amount of the IAP gene expressed in a PBMN or a T cell, such as for example, an amount of IAP mRNA or an amount of an IAP protein.

As used herein, the term "biomarker" is intended to mean a detectable level of either an IAP mRNA or an IAP protein in such a pattern characterizing a specific MS subtype.

As used herein, the term "multiple sclerosis subtype" is intended to mean one or more of four categories of multiple sclerosis and includes relapsing-remitting (RRMS), secondary-progressive (SPMS), primary progressive (PPMS) and benign. The term "relapsing-remitting multiple sclerosis" can be further categorized into quiescent relapsing-remitting multiple sclerosis (RRQ) and active relapsing-remitting multiple sclerosis (RRA).

As used herein, the term "aggressive form of multiple sclerosis" is intended to mean RRA and SPMS.

As used herein, the term "control subjects" is intended to mean subjects who are healthy normal, or who have been diagnosed as having benign MS.

We have unexpectedly discovered distinct patterns of IAP mRNA and IAP protein level expression in whole blood, peripheral blood mononuclear cells (PBMN) and resting T cells from healthy subjects and patients with benign MS, quiescent RRMS (RRQ), active RRMS (RRA), SPMS or PPMS. Taken together, these results demonstrate that patterns of IAP expression in whole blood, PBMN and resting T cells can be used to differentiate between, and are diagnostic of, sub-types of MS. Thus, we can now design new (non-MRI based) diagnostic tests for MS based on the detection of the IAP gene expression levels and that these genes may serve as surrogate biomarkers for therapeutics based on the treatment of MS by the induction of apoptosis in auto-reactive immune cells.

Accordingly in an embodiment of the present invention, there is provided a method for differentiating between multiple sclerosis subtypes in a patient, the method comprising: a) determining an amount of an IAP gene expression level in a blood sample obtained from the patient; and b) correlating the amount of the IAP gene expression level in the blood sample with the presence of a multiple sclerosis subtype in the patient. For example, the IAP gene expression level is compared to those of control subjects in which an increase in the IAP gene expression level relative to those of the control subjects indicates that the patient is suffering from one of the MS subtypes. The MS subtypes include benign MS, quiescent relapsing remitting MS, active relapsing remitting MS, primary progressive MS or secondary progressive MS. The control subjects are those subjects who have been previously diagnosed as having benign MS or are healthy normal subjects.

The invention provides for quantitative detection and determination of the IAP gene expression levels by measuring either the levels of transcribed IAP mRNA or the level of IAP protein in the blood sample. One skilled in the art will recognize that many techniques are available to measure the levels of the aforesaid IAP gene expression levels. The IAP genes encode an IAP protein selected from NAIP, XIAP, HIAP-1, HIAP-2 or survivin. In one example, IAP mRNA is measured using quantitative real time polymerase chain reaction (qRT-PCR), which is described in more detail below, whereas IAP protein level is measured using an immunoassay.

Immunoassays for example include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, fluorescent immunoassays and the like. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding an antibody of interest to the cell lysate, incubating for a period of time (e.g., 1-4 hours) at 4 degrees C., adding protein A and/or protein G sepharose beads to the cell lysate, incubating for about an hour or more at 4 degrees C., washing the beads in lysis buffer and re-suspending the beads in SDS/sample buffer. The ability of the antibody to immunoprecipitate a particular antigen can be assessed by, e.g., western blot analysis. One skilled in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One skilled in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen (i.e. an IAP polypeptide biomarker), coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One skilled in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

In one example, peripheral blood mononuclear (PBMN) cells and T cells are typically isolated from the blood samples of the patients and are analyzed for IAP gene expression levels as is described in more detail below. The IAP gene expression levels are compared to those of the control subjects, an increase in the IAP gene expression level relative to those of the control subjects indicates that the patient is suffering from one of the MS subtypes described above.

Detection of certain IAP gene biomarkers are diagnostic of the specific subtype of MS. For example, in MS patients with RRA (but not RRQ) and SPMS, XIAP mRNA and protein levels were selectively elevated in PBMN cells relative to normal control subjects or patients with benign or PPMS. HIAP-2 mRNA was elevated in PBMN cells of patients with RRA and SPMS relative to normal control subjects and patients with a benign MS disease course. In T cells, HIAP-2 mRNA levels were elevated in patients with RRMS irrespective of disease activity and SPMS relative to normal control subjects. The expression of HIAP-1 was selectively elevated in resting T cells from RRMS patients irrespective of disease activity relative to all other experimental groups. In PPMS patients, survivin expression was elevated in T cells relative to normal control subjects, RRMS and SPMS patients.

Distinguishing Between Specific MS Subtypes

As illustrated in Table 3 below, the diagnostic methods of the invention can be used to differentiate between specific MS subtypes. For example, in one alternative aspect of the invention, there is provided a method for distinguishing between quiescent and active forms of relapsing remitting multiple sclerosis in a patient. The method comprises determining the amount of XIAP and HIAP-2 gene expression levels in peripheral blood mononuclear (PBMN) cells obtained from the patient. The amount of XIAP and HIAP-2 gene expression levels are compared to XIAP and HIAP-2 gene expression levels of control subjects, an increase in the gene expression levels coupled with clinical presentation being an indication that the patient is suffering from active relapsing remitting multiple sclerosis. In addition, there is also provided a method for distinguishing secondary progressive multiple sclerosis in a patient. In this case, the method comprises determining an amount of XIAP and HIAP-2 gene expression levels in peripheral blood mononuclear (PBMN) cells obtained from the patient. The amount of the XIAP and HIAP-2 gene expression levels are compared to these gene expression levels of control subjects, an increase in the XIAP and HIAP-2 gene expression levels being an indication that the patient is suffering from secondary progressive multiple sclerosis.

In another alternative aspect, there is provided a method for differentiating quiescent relapsing remitting multiple sclerosis in a patient. In this case, the method comprises determining an amount of HIAP-1 gene expression level is determined in T cells obtained from the patient. The amount of the HIAP-1 gene expression level in the T cells is compared to the HIAP-1 gene expression levels of control subjects, an increase in the HIAP-1 gene expression levels being an indication that the patient is suffering from quiescent relapsing remitting multiple sclerosis.

In addition, there is provided a method for differentiating active relapsing remitting multiple sclerosis in a patient. In this case, the method comprises determining an amount of HIAP-1 and HIAP-2 gene expression levels in T cells obtained from the patient. The amount of the HIAP-1 and HIAP-2 gene expression levels in the T cells is compared to the HIAP-1 and HIAP-2 gene expression levels of control subjects, an increase in the HIAP-1 and HIAP-2 gene expression levels being an indication that the patient is suffering from active relapsing remitting multiple sclerosis.

In certain circumstances, where a clinician suspects that a patient has RRMS, but is uncertain as to whether the RRMS is quiescent or active, there is provided a method for differentiating between quiescent and active relapsing remitting multiple sclerosis in a patient. This method comprises determining an amount of HIAP-1 and HIAP-2 gene expression levels in T cells obtained from the patient. The amount of the HIAP-1 and HIAP-2 gene expression levels in the T cells is compared to the HIAP-1 and HIAP-2 gene expression levels of control subjects. An increase in only HIAP-1 gene expression levels is an indication that the patient is suffering from quiescent relapsing remitting multiple sclerosis, whereas an increase in both the HIAP-1 and HIAP-2 gene expression levels is an indication that the patient is suffering from active relapsing remitting multiple sclerosis.

In another alternative aspect of the present invention, there is provided a method for differentiating secondary progressive multiple sclerosis in a patient. In this case, the method comprises determining an amount of HIAP-2 gene expression level in T cells obtained from the patient. The amount of the HIAP-2 gene expression level in the T cells is compared to the HIAP-2 gene expression levels of control subjects, an increase in the HIAP-2 gene expression levels being an indication that the patient is suffering from secondary progressive multiple sclerosis.

In another alternative aspect of the present invention, there is provided a method for differentiating primary progressive multiple sclerosis in a patient. In this case, the method comprises determining an amount of survivin gene expression level in T cells obtained from the patient. The amount of the survivin gene expression level in the T cells is compared to the survivin gene expression levels of control subjects, an increase in the survivin gene expression levels being an indication that the patient is suffering from primary progressive multiple sclerosis.

Currently, benign MS cannot be distinguished from other types of MS, including relapsing remitting MS relapsing remitting MS, primary progressive MS or secondary progressive MS. In patients who first present themselves to a clinician, no diagnostic tests are available to distinguish the benign MS from quiescent relapsing remitting MS. It would therefore be advantageous to distinguish between benign MS and the other types of MS to prevent un-needed treatment of the benign MS patients with interferon drugs. We have shown that NAIP expression is the only biomarker in which there is an increase in whole blood. RRQ, RRA and SPMS relative to normal healthy subjects. There was no difference in benign or PPMS whole blood NAIP. In T cells, a subset of PPMS patients showed an increase in NAIP mRNA expression.

Thus, according to another aspect of the present invention, there is provided a method for differentiating between benign and either relapsing remitting MS, primary progressive MS or secondary progressive MS in a patient. In this case, the method comprises determining an amount of NAIP gene expression levels in whole blood obtained from the patient. The NAIP gene expression levels are then compared to the amount of NAIP gene expression levels in control subjects, an increase in the NAIP gene expression levels being an indication that the patient is suffering from either relapsing remitting MS, primary progressive MS or secondary progressive MS and not benign MS.

Determination of a Patient's Suitability for Interferon Drug Treatment

One advantage of the methods of the present invention concern a clinician's ability to appropriately treat MS sufferers with interferon drugs, such as Rebif 22, Rebif 44, Avonex, and Betaseron. In instances where such treatment is inappropriate, such as in patients suffering from benign MS or PPMS, the clinician may now first screen patients to eliminate those for which treatment would be inappropriate. Thus, according to an alternative aspect of the present invention, there is provided a method of testing a patient's suitability for interferon-$\beta$ treatment of multiple sclerosis. This method comprises determining an amount of an IAP gene expression level in a blood sample obtained from the patient suspected of having an aggressive subtype of multiple sclerosis. The amount of the IAP gene expression level can then be compared to the IAP gene expression levels of control subjects, an increase in IAP gene expression levels being an indication that the patient is suffering from an aggressive subtype of multiple sclerosis, the patient being suitable for treatment with interferon-$\beta$.

For those patients for which interferon therapy is appropriate, one aspect of the invention would be a method for monitoring the progress of a multiple sclerosis therapy of a patient. This method comprises determining an amount of an IAP gene expression level in a first blood sample obtained from the patient at first time period, followed by determining an amount of the IAP gene expression level in a second blood sample obtained from the patient at a second time period. The difference between the two time periods who be determined by the type of therapy used by the clinician and how quickly the patient is progressing. The IAP gene expression levels would be compared and a decrease in the IAP gene expression level at the second time period being an indication that the patient is responding to the multiple sclerosis therapy. The therapy could be continued until the IAP gene expression is significantly diminished or essentially eliminated.

For those patients who present clinical symptoms of active relapsing remitting MS, it is advantageous to determine whether the patient is at risk of developing secondary progressive MS. Thus, another alternative embodiment of the present invention provides a method of identifying whether a patient is at risk of developing secondary progressive multiple sclerosis from active relapsing remitting multiple sclerosis, the method comprising: a) obtaining a blood sample for the patient; and b) comparing XIAP mRNA levels in PBMNs, and HIAP-1 and HIAP-2 mRNA levels in T cells, with those of a control subject, elevated XIAP mRNA levels in the PBMNs, elevated HIAP-2 mRNA levels in the T cells, and normal HIAP-1 levels in the T cells, being an indication that the patient is at risk of developing secondary progressive MS. Furthermore, the aforesaid alternative method may further include detecting a normalization of HIAP-1 in T cells. Such a change would suggest initiation of more aggressive treatments such as Tysabri®.

II: Diagnostic Kits

Generally, speaking a clinician's office may be adapted to aid quick and reliable diagnosis of a patient suspected of having one of the above mentioned subtypes of MS. Thus, according to one embodiment of the invention, there is provided a diagnostic kit for diagnosing a patient suspected of having a subtype of multiple sclerosis. The kit comprises a vessel or vessels for receiving a blood sample taken from the subject, an agent that specifically detects IAP protein or amplifies IAP mRNA; and printed instructions for detecting the IAP protein or the amplified IAP mRNA in the sample.

For example, the kits can be used to detect any one or more of the IAP gene expression levels, such as IAP mRNA or IAP polypeptide described herein, which biomarkers are differentially present in samples of a patient and normal subjects. The kits of the invention have many applications. For example, the kits can be used to differentiate if a subject has benign MS, quiescent or active relapsing remitting MS, primary progressive MS or secondary progressive MS. In another example, the kits can be used to identify compounds that modulate expression of one or more of the markers in in vitro or in vivo animal models to determine the effects of treatment.

The IAP protein is detected using immunoassays as described above.

In one example, a kit comprises (a) an antibody that specifically binds to an IAP polypeptide; and (b) a detection agent. Such kits can be prepared from the materials described in U.S. Pat. No. 5,919,912.

In the case of IAP mRNA, the agent for amplifying the IAP mRNA are the primers and probes selected from Table 2 below. In some instances, the kit may further comprise instructions for suitable operation parameters in the form of a label or a separate insert.

The invention also includes a diagnostic kit which includes a substantially isolated antibody specifically immunoreactive with IAP polypeptide antigens, and means for detecting the binding of the polypeptide antigen to the antibody. In example, the antibody is attached to a solid support. In a specific example, the antibody may be a monoclonal antibody. The detecting means of the kit may include a second, labeled monoclonal antibody. Alternatively, or in addition, the detecting means may include a labeled, competing antigen.

Optionally, the kit may further comprise a standard or control information so that a test sample can be compared with a control information standard to determine if the test amount of a marker detected in a sample is indicative of a MS subtype in a patient clinically diagnosed with MS.

Optionally, the kit can further comprise instructions for suitable operational parameters in the form of a label or a separate insert. For example, the kit may have standard instructions informing a consumer how to wash a probe after a sample is contacted on the probe. In another example, the kit may have instructions for pre-fractionating a sample to reduce complexity of IAP proteins in the sample. In another example, the kit may have instructions for automating the fractionation or other processes.

The methods described above and below may also be carried out on patient blood samples, which may have been obtained and stored according to methods known to those skilled in the art of blood sample handling and storage. Thus it is within the scope of the present invention to provide a method of differentiating between multiple sclerosis subtypes in a patient blood sample. In this case, the method comprises determining an amount of an IAP gene expression level in the blood sample, as described above, and then correlating the amount of the IAP gene expression level in the blood sample with the presence of a multiple sclerosis subtype.

Materials and Methods

The following examples are offered by way of illustration, not by way of limitation. While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined not with reference to the above description, but instead should be determined with reference to the appended claims along with their full scope of equivalents.

Unless otherwise stated, the following abbreviations are used throughout:

CNS=central nervous system;
CSF=cerebral spinal fluid;
EDSS=Expanded Disability Status Scale;
HIAP-1=human inhibitor of apoptosis protein-1;
HIAP-2=human inhibitor of apoptosis protein-2;
IAP=inhibitor of apoptosis protein;
MRI=Magnetic Resonance Imaging;
MS=multiple sclerosis;
NAIP=neuronal apoptosis inhibitor protein;
PBMN cells=peripheral blood mononuclear cells;
RR=relapsing-remitting;
RRQ=relapsing-remitting quiescent disease activity;
RRA=relapsing-remitting active disease;
RRMS=relapsing remitting Multiple Sclerosis,
SP=secondary-progressive;
SPMS=secondary-progressive Multiple Sclerosis;
PP=primary progressive;
PPMS=primary-progressive Multiple Sclerosis;

qRT-PCR=quantitative reverse transcriptase polymerase chain reaction; and

XIAP=X-linked inhibitor of apoptosis protein.

I. Patient Selection and Blood Sampling

Qualified clinical personnel obtained blood samples from MS patients with Benign (n=12), RRMS (n=24), SPMS (n=22) and PPMS (n=19) during the patients regularly scheduled visit to the Dalhousie Multiple Sclerosis Research Unit (DMSRU). Research and clinical personnel recruited 14 healthy volunteer subjects from the community. All subjects gave informed consent prior to blood draw. A practicing neurologist with a special interest in MS (VB) at the DMSRU prior to study entry diagnosed all patients with definite MS according to established diagnostic criteria [McDonald et al. 2001] and determined each individual patient's level of disability and disease progression employing the EDSS. Benign MS was characterized in patients that had disease duration of more than 10 years and an EDSS of 2.0 or less or in patients with disease duration of greater than 15 years and an EDSS 3.0 or less. Relapsing-remitting MS quiescent disease state (RRQ) was characterized in patients that did not experience any relapses within the last 2 years and did not experience EDSS progression over the same time period. Relapsing-remitting MS active disease state (RRA) was characterized in patients that had experienced 1 or more relapses in the last year or gadolinium positive ($Gd^+$) lesions on recent MRI. Patients were diagnosed as having secondary-progressive MS (SPMS) following a previous diagnosis of RRMS but were currently experiencing progression of disability with or without concurrent relapses. In comparison to RRMS most SPMS patients have an EDSS greater than 4 and often greater than 6 as compared to the usual EDSS course associated with RRMS. Primary progressive MS (PPMS) was diagnosed in patients that displayed a progressive, non-phasic neurological syndrome. Most patients presented as a spinal cord syndrome or a cerebellar dysfunction coupled with $Gd^+$ lesions disseminated in space and time by MRI criteria with continued clinical progression for at least one year, according to the revised McDonald diagnostic criteria [Polman et al. 2005]. Patients and normal control subjects were included if they were 18 years of age or older, had no other major medical illness and gave written informed consent. Subjects did not receive corticosteroid or immune suppressive therapy within 3 months prior to blood draw. Subject profiles are presented in Table 1

Thirty-seven milliliters of blood was collected in four 8 ml BD Vacutainer® sodium citrate Ficoll gradient tubes and two 2.5 ml Paxgene (Qiagen) whole blood RNA tubes. Our investigation sought to determine not only if IAP levels were differentially affected in specific subtypes of MS, but also whether these changes in IAP expression could be detected in whole blood or peripheral blood mononuclear (PBMN) cells in addition to resting T lymphocytes. The blood samples were immediately transported at room temperature to the Good Laboratory Practice (GLP) Accredited hematology laboratory at the Queen Elizabeth Hospital, centrifuged at high speeds, and the PBMN cells and T lymphocytes isolated from whole blood employing negative selection and stored at −80° C. until RNA and protein extraction.

II. RNA Expression, Cell Purification, RNA Amplification and Statistical Analyses A. Whole Blood Blood was collected in two 2.5 ml Paxgene RNA tubes, as last blood-draw following collection in the 4 Ficoll-Gradient blood tubes (below). Tubes were inverted several times to mix and left at room temperature (RT) for 24 hours. Following the 24-hour RT incubation period tubes were centrifuged at 3400×g in a swinging bucket centrifuge for 10 minutes to pellet nucleic acids. The pellets were washed, resuspended, and incubated in optimized buffers containing Proteinase K to digest proteins followed by a second centrifugation step to remove residual cell debris. The supernatant was transferred to a fresh microcentrifuge tube, ethanol added and the lysate applied to a Paxgene RNA spin column. The column was washed and treated with RNAse-free DNAse (Qiagen) and then pure RNA eluted according to the manufacturer's protocols (Qiagen). Total RNA yields were measured by ultraviolet (UV) absorbance and overall RNA quality was assessed by gel electrophoresis and staining for visualization of RNA band integrity. RNA samples were diluted in RNAse free water to give a final concentration of 10 ng/μl, prior to analysis of IAP gene expression by qRT-PCR.

B. Isolation of RNA from Peripheral Blood Mononuclear Cells (PBMN) and T Lymphocytes Whole blood is made up of a heterogeneous population of erythrocytes, granulocytes, and other peripheral blood mononuclear (PBMN) cells that make it difficult to detect differential IAP gene and protein expression that may occur in only a subset of immune cell types. As such, in addition to blood collection in Paxgene whole-blood RNA tubes, thirty-two ml of blood was collected in four 8 ml Ficoll-gradient tubes from each subject to isolate mononuclear cells, including T and B lymphocytes as well as monocytes/macrophages. Two of the tubes for each subject were used to isolate PBMN cells and two of the tubes were used to isolate resting (i.e. unactivated;

TABLE 1

| MS Subtype | Gender | Ave. Age ± S.D. | Ave. EDSS ± S.D. | Ave. Disease Duration (years) | # Patients On DMT | Ave. Years on DMT ± S.D. |
|---|---|---|---|---|---|---|
| NS | 10 F; 9 M | 39.7 ± 11.8 | n/a | n/a | n/a | n/a |
| Benign | 14 F; 4 M | 54.1 ± 6.4 | 1.8 ± 1.0 | 23.7 ± 6.1 | 0 | 6.3 ± 2.1 |
| RRQ | 15 F; 1 M | 48.6 ± 7.9 | 2.5 ± 1.3 | 12.9 ± 6.9 | 12 | 3.0 ± 2.2 |
| RRA | 11 F; 4 M | 42.1 ± 7.8 | 2.9 ± 1.5 | 9.3 ± 9.3 | 6 | 2.6 ± 2.8 |
| SP | 18 F; 6 M | 55.3 ± 9.4 | 6.0 ± 1.3 | 22.6 ± 9.0 | 12 | 5.2 ± 2.3 |
| PP | 20 F; 11 M | 57.7 ± 9.5 | 5.9 ± 1.9 | 17.8 ± 12.3 | 0 | n/a |

NS = normal control subjects; Benign = Benign MS; RRQ = RRMS quiescent disease activity RRA = RRMS active disease activity; SP = SPMS; PP = PPMS; F = female; M = male; Ave. = average; S.D. = standard deviation; DMT = disease modifying therapy (Rebif 22, Rebif 44, Avonex, Betaseron, Copaxone).

not mitogen activated) T lymphocytes. For the isolation of highly purified T lymphocytes ($2\times10^5$) from whole blood of MS patients by negative selection (StemCell Technologies, Vancouver, BC) four hundred microliters (μL) of Rosette-SepT (Stem Cell Technologies) was added to two of the four Ficoll-gradient tubes (Becton, Dickinson and Company; BD Vacutainer® CPT™ Cell Preparation Tube with Sodium Citrate) and incubated at room temperature for 20 minutes. Negative selection was chosen over positive selection in order to minimize T cell activation. For the isolation of PBMN cells, RosetteSep T was withheld. All tubes were inverted twice to mix and centrifuged at 1650-1800×g for 25 minutes in a swinging bucket centrifuge. The T cells and PBMN cells were pipetted off into separate 15 ml conical centrifugation tubes, treated with ammonium chloride (StemCell Technologies, Vancouver, B.C.) for 10 minutes on ice to remove any remaining red blood cells, and centrifuged at 1000×g for 10 minutes in a swinging bucket centrifuge to pellet the cells. The red blood cells (RBC) and polynuclear cells, including the neutrophils, the most abundant of the white blood cells [Biswas et al. 2003; Stroncek et al. 1997] were destroyed. Cell pellets were washed twice in phosphate buffered saline/fetal bovine serum and stored at −80° C. until RNA and protein extraction. In most cases, pending difficulties in blood withdrawal (i.e. vein collapsed) or tube breakage, two T cell pellets and two PBMN cell pellets were obtained for each subject. Total RNA was extracted from one T cell pellet and one PBMN cell pellet from each patient using the Qiagen RNeasy kit (Mississauga, Ontario) according to the manufacturer's instructions. All sample preparations included RNAse-free DNAse treatment. Total RNA yields were measured by UV absorbance. RNA samples were diluted in RNAse free water to give a final concentration of 10 ng/μl.

III. Quantitative RT-PCR

Quantitative RT-PCR was performed to confirm changes in NAIP, XIAP, HIAP-1, HIAP-2 and survivin gene expression in patients with different subtypes of MS relative to normal control subjects. Aegera Therapeutics Inc. provided Taqman probes and Taqman primers for the IAPs. Total RNA (50 ng) isolated from whole blood, PBMN or T cells was reverse transcribed to yield first-strand cDNA and amplified using the Taqman one-step EZ RT-PCR Core reagents kit (Applied Biosystems, Foster City, Calif., USA). For detection of each IAP, forward and reverse primers were used at a concentration of 600 nmol/L and all the Taqman fluorogenic probes at a concentration of 200 nmol/L. The expression of beta β2 microglobulin was used as an endogenous control reference (Applied Biosystems, Foster City, Calif., USA). β2 microglobulin was amplified using Taqman β2 Microglobulin Control Reagents Kit (Applied Biosystems, Foster City, Calif., USA). The Taqman probe and primer sequences for the IAPs are presented in Table 2. All amplifications were done in triplicate within the same 96 well plate and threshold cycle (CT) scores were averaged for subsequent calculations of relative expression values. The CT scores represent the cycle number at which the fluorescence signal (ΔRn) crossed an arbitrary (user-defined) threshold. Data was extracted and amplification plots generated with MJ Research Inc. (USA) software. Quantification of IAP gene expression relative to β2 microglobulin was calculated according to the experimental protocol's $2^{-\Delta\Delta CT}$ method [Livak and Schmittgen 2001]. After the PCR amplification was finished the data were analyzed using the software provided by MJ Research and then the analyzed data was exported into an Excel/SPSS spreadsheet for further statistical analysis. Results were expressed in Fold increase or Relative to a "calibrator." The calibrator sample was the RNA sample from a normal age-matched female subject. For amplicons designed and optimized according to the Applied Biosystems guidelines (amplicon size<150 bp), the efficiency is close to one. Therefore, the amount of target, normalized to an endogenous reference (i.e., β2 microglobulin) and relative to a calibrator (i.e., normal control RNA), is given by $2^{-\Delta\Delta CT}$, where CT=Cycle Threshold (fractional cycle number at which the amount of amplified target reaches a fixed threshold), ΔCT=CT, X−CT, R (difference in threshold cycles for target and reference) and ΔΔCT=ΔCT (target)−ΔCT (calibrator value). ΔΔCT scores for the IAP mRNAs for each sample were subjected to separate one-way analysis of variance (ANOVA) assessing the level of expression of each of the genes among patients with different types of MS (Benign, RR, SP, PP) and normal controls. The ΔΔCT scores for the IAP mRNAs for RRMS patients were assessed according to disease activity (RRQ or RRA) at the time of blood draw. Graphpad Prism 4 (San Diego, Calif., USA) and SPSS 11.0 (SPSS, Inc., Chicago, Ill., USA) software were used for all statistical analyses. Individual group differences following significant ANOVA (α=0.05) results were analyzed using Tukey's honestly significant differences (HSD) or least significant differences (LSD) where appropriate. Parametrical analysis using the Pearson product moment correlation coefficient was employed to assess the relationship between IAP levels and EDSS scores of MS patients. Non-parametrical analysis using the Spearman rank correlation coefficient was employed to assess the relationship between MS disease subtype and EDSS scores. Normal subjects were included in the analysis with an EDSS score of 0 indicative of normal neurological function.

TABLE 2

| Human IAP | Forward and Reverse Primer and Probe Sequences |
|---|---|
| XIAP | Forward 5'-GGT GAT AAA GTA AAG TGC TTT CAC TGT-3' (SEQ ID NO: 1) <br> Reverse 5'-TCA GTA GTT CTT ACC AGA CAC TCC TCA A-3' (SEQ ID NO: 2) <br> Probe 5'-(FAM)CAA CAT GCT AAA TGG TAT CCA GGG TGC AAA TAT C(TAMRA)-3' (SEQ ID NO: 3) |
| HIAP-1 | Forward 5'-TGG AGA TGA TCC ATG GGT TCA-3' (SEQ ID NO: 4) <br> Reverse 5'-GAA CTC CTG TCC TTT AAT TCT TAT CAA GT-3' (SEQ ID NO: 5) <br> Probe 5'-(FAM)CTC ACA CCT TGG AAA CCA CTT GGC ATG(TAMRA)-3' (SEQ ID NO: 6) |
| HIAP-2 | Forward 5'-TCT GGA GAT GAT CCA TGG GTA GA-3' (SEQ ID NO: 7) <br> Reverse 5'-TGG CCT TTC ATT CGT ATC AAG A-3' |

TABLE 2-continued

| Human IAP | Forward and Reverse Primer and Probe Sequences |
|---|---|
| | (SEQ ID NO: 8)<br>Probe 5'-(FAM)CTC ACA CCT TGG AAA CCA CTT GGC ATG(TAMRA)-3'<br>(SEQ ID NO: 9) |
| Survivin | Forward 5'-TCT GCT TCA AAG AGC TGG AA-3'<br>(SEQ ID NO: 10)<br>Reverse 5'-GAA AGG AAA GCG CAA CC G-3'<br>(SEQ ID NO: 11)<br>Probe 5'-(FAM)AGC CAG ATG ACG ACC CCA TAG AGG AAC ATA(TAMRA)-3'<br>(SEQ ID NO: 12) |
| NAIP | Forward 5'-GCC ATT TTA TGT CCA AGG GAT ATC-3'<br>(SEQ ID NO: 13)<br>Reverse 5'-CTT CCC AAT TTC CTA AAC ACT CA-3'<br>(SEQ ID NO: 14)<br>Probe 5'-(FAM)CTG TAC CGT GTC CTG TTT ACC TGT AAA GAC AAA GC(TAMRA)-3'<br>(SEQ ID NO: 15) |

IV. Protein Purification, Protein Expression and Quantification

Results from our gene profiling studies were complimented and cross-validated by determining whether there were corresponding increases in the encoded proteins. In brief, T cells were isolated by negative selection from 8 mL of blood as described above. T cells and PBMN cells were lysed with radioimmunoprecipitation assay (RIPA) lysis buffer with complete protease inhibitor (Roche) and incubated on ice for 10 minutes. Cell lysates were centrifuged at 12000 rpm in an eppendorf microcentrofuge at 4° C. for 20 minutes. The supernatant was extracted and transferred to a new tube. Small aliquots (2 µL) were used to determine protein concentrations of the individual patient samples using the BCA protein assay method (Pierce, Rockford, Ill., USA). Supernatants were diluted 1:1 with 2× sodium dodecyl sulfate (SDS) sample buffer with reducing agent dithiothreitol (DTT) (Sigma, D-9779) and kept at −80° C. until analyses.

Twenty µg of protein was loaded on a 12% polyacrylamide gel, separated by SDS-PAGE and transferred at 100 volts for 120 minutes to an Immobilin-P (polyvinylidene fluoride) membrane (Millipore, Biorad Laboratories, Mississauga, Ontario, Canada). Membranes were blocked for 2 hours at room temperature (RT) in 5% skim milk powder in tris-buffered saline (TBS)/0.05% polyoxyethylenesorbitan monolaurate (Tween-20) (Sigma, Canada). Membranes were probed with XIAP (1:250; BD Pharminogen), HIAP-1 (1:250; BD Pharminogen), HIAP-2 (1:250; BD Pharminogen) or survivin (1:250; Novus Biologicals) overnight at 4° C. Membranes were washed in TBS/0.05% Tween-20 and reprobed with an IgG anti-mouse peroxidase (1:10 000) labeled antibody (Vector laboratories). Chemiluminescence was detected by autoradiography with Hyperfilm ECL™ high performance chemiluminescence film (Amersham Pharmacia Biotech, England) and bands were quantified by analysis of scanned images by Kodak 1D Scientific Imaging software (Kodak, USA). Several film exposures were obtained for each protein investigated to make certain that optical density signals were within a linear range, permitting accurate quantification. Blots were then stripped (Reblot, Chemicon) and reprobed for the endogenous control protein β-Actin (1:10 000; Sigma, Canada) to ensure equal protein loading employing a peroxidase anti-mouse secondary antibody (1:10 000 Vector laboratories). Chemiluminescence was detected as described above.

The optical density scores were subjected to a one-way ANOVA assessing the relative protein expression of each of the IAPs in the different MS patient groups (Benign, RRQ, RRA, SP, PP) and normal controls. The optical density scores for the IAPs for RRMS patients were assessed according to disease activity (active or quiescent) at the time of blood draw. The inclusion of disease activity was used to assess the protein expression profiles of the IAPs from PBMN cells or T cells from RRMS patients to determine whether the expression of specific proteins was related to disease course. Individual group differences following significant ANOVA ($\alpha=0.05$) results were analyzed using Tukey's honestly significant differences (HSD) or least significant difference (LSD) multiple comparisons where appropriate. It should be mentioned that although the aim of this investigation was to analyze 3 different RNA preparations from the same subject (i.e. whole blood, PBMN cells and T cells) along with the corresponding protein (PBMN cells and T cells) most, but not all (~70%), patients are represented in the three 3 types of RNA samples and 2 types of protein samples due most commonly to low RNA and protein yields, especially with respect to T cell samples.

Results

Patient Demographics and Past Clinical History

The Dalhousie Multiple Sclerosis Research Unit (DM-SRU) is the sole regional specialty clinic for MS in Nova Scotia and maintains clinical records and a database on all patients seen since 1979. The DMSRU database provides a detailed clinical history of the majority of MS patients in Nova Scotia (Bhan et al., 2005) permitting clinical features and biochemical markers (mRNA, proteins) derived from blood samples to be correlated. Patients in the present study first presented to the DSMRU as early as 1980. All patients included in this study, presented to the DMSRU with a RR, RR progressive or primary progressive disease activity. At this time, patients with RR progressive or primary progressive disease activity displayed higher scores on Kurtzke pyramidal ($F(2, 94)=38.74$, $p<0.0001$) and bowel and bladder scales ($F(2, 94)=9.432$, $p<0.0001$), while patients with primary progressive disease activity also displayed elevated cerebellar symptom contributions ($F(2, 94)=3.162$, $p<0.05$) relative to RR disease course.

The presentation of neurological symptoms of patients included in the present study were obtained from the DSMRU database and revealed several specific clinical characteristics that distinguished patients that come to display a progressive MS disease course (SPMS and PPMS) from patients with present-day benign, RRQ or RRA MS. Clinical histories of the various MS patients revealed that patients that presented to the clinic with pyramidal ($F(4, 95)=8.576$, $p<0.0001$) or bowel/bladder ($F(4, 95)=3.53$, $p=0.01$) dysfunction as measured by the Kurtzke pyramidal or bowel and bladder score (0-6), indicative of motor cortical and spinal cord deficits, would later develop a progressive disease course (SP or PPMS). The frequency of initial symptom presentation in patients that would be at the present date diagnosed with benign, RRQ, RRA, SP or PP are as follows: Benign: frequent presentation with brainstem (45%), cerebellar dysfunction (15 %), spinal cord (95%), cerebral-pyramidal symptoms (0%) and optic neuritis (25%); RRQ: frequent presentation with brainstem (20%), cerebellar dysfunction (20%), spinal cord (100%), cerebral-pyramidal symptoms (0%) and optic neuritis (20%); RRA: frequent presentation with brainstem (53%), cerebellar dysfunction (0%), spinal cord (66%), cerebral-pyramidal symptoms (6%) and optic neuritis (43%); SPMS: frequent presentation with brainstem (42%), cerebellar dysfunction (29%), spinal cord (100%), cerebral-pyramidal symptoms (9%) and optic neuritis (33%); PPMS: frequent presentation with brainstem (33%), cerebellar dysfunction (19%), spinal cord (96%), cerebral-pyramidal symptoms (4%) and optic neuritis (30%).

Expanded Disability Status Scale (EDSS)

There was a strong correlation ($r=0.833$, $p<0.0001$) between EDSS score and MS disease subtype. Patients with SPMS (range 2.5 to 7.5) or PPMS (range 2 to 8.5) displayed higher EDSS scores than patients with benign MS (range 0 to 3) or RRMS that were categorized as either quiescent (range 1 to 6) or active (range 1.5 to 6).

qRT-PCR

A. Whole Blood

There were no differences in XIAP (FIG. 1A), HIAP-1 (FIG. 2A), HIAP-2 (FIG. 3A), or survivin (FIG. 4A) mRNA levels in RNA extracted from whole blood (ANOVA, $p>0.05$) among normal control subjects (NS), or patients with benign, RRQ, RRA, SP or PPMS [XIAP $F (4, 66)=1.552$, $p=0.1974$; HIAP-1 $F (4, 70)>1$, $p=0.605$, HIAP-2 $F (4,69)=1.421$, $p=0.236$, and survivin $F (4, 61)=1.448$, $p=0.229$, respectively].

B. PBMN Cells

Figure 2:
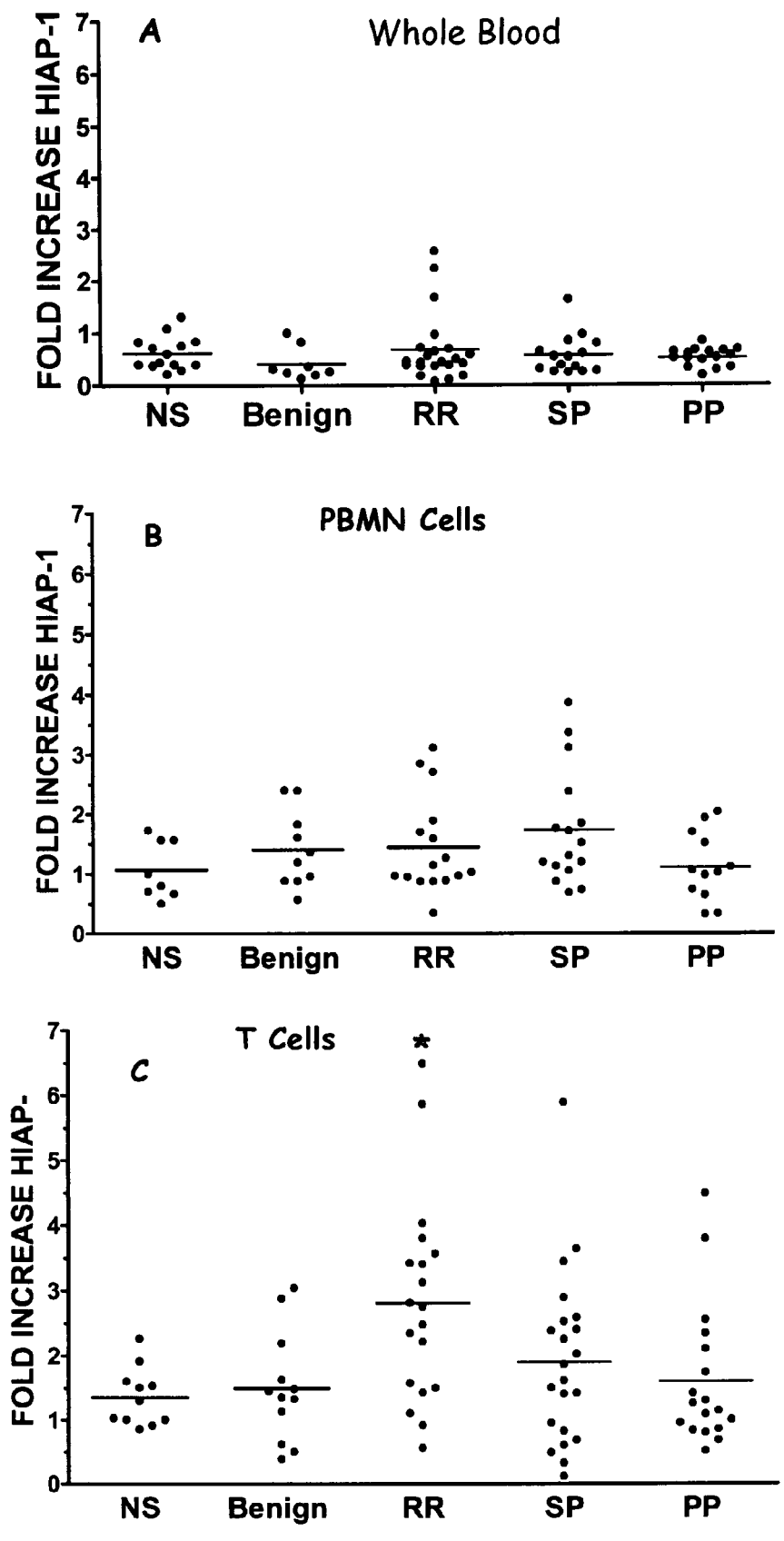
FIGS. 2A to 2C are graphs illustrating the relative quantification of HIAP-1 mRNA expression in RNA extracted from (A) whole blood, (B) PBMN cells and (C) T cells employing qRT-PCR. The graphs depict the expression of HIAP-1 mRNA relative to the expression of the endogenous control gene $\beta_2$ microglobulin ($2^{-\Delta\Delta CT}$) in normal subjects (NS) and patients with benign, Relapsing-Remitting (RR), Secondary-Progressive (SP) or Primary-Progressive (PP) MS patients. Quiescent (Q)=MS symptoms in remission at time of blood draw and the patient has not experienced any relapses in the 2 years prior to blood draw; Active (A)=MS symptoms are active at time of blood draw and the patient has experienced at least one relapse in the 2 years prior to blood draw. (A) HIAP-1 gene expression in whole blood was not affected in MS relative to NS. (B) There appears to be no change in HIAP-1 gene expression in PBMN cells of MS patients relative to NS. (C) In contrast to XIAP gene expression levels in T cells, HIAP-1 gene expression is increased in T cells of RRMS patients irrespective of disease activity (RRQ and RRA) relative to NS and patients with benign and PPMS. *p<0.05.
Figure 3:
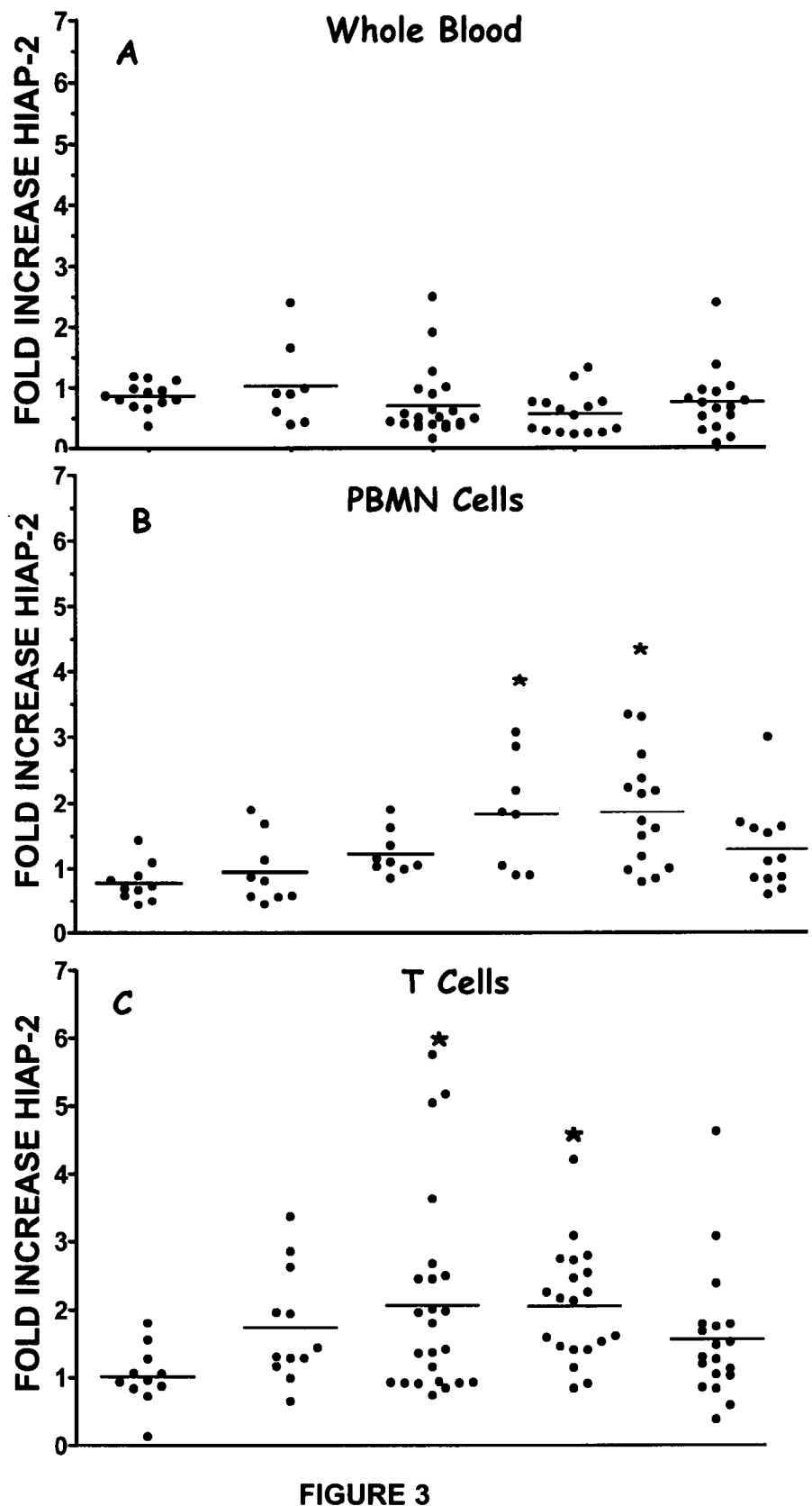
FIGS. 3A to 3C are graphs illustrating the relative quantification of HIAP-2 mRNA expression in RNA extracted from (A) whole blood, (B) PBMN cells and (C) T cells employing qRT-PCR. The graphs depict the expression of HIAP-2 mRNA relative to the expression of the endogenous control gene $\beta_2$ microglobulin ($2^{-\Delta\Delta CT}$) in normal subjects (NS) and patients with benign, Relapsing-Remitting (RR), Secondary-Progressive (SP) or Primary-Progressive (PP) MS patients. Quiescent (Q)=MS symptoms in remission at time of blood draw and the patient has not experienced any relapses in the 2 years prior to blood draw; Active (A)=MS symptoms are active at time of blood draw and the patient has experienced at least one relapse in the 2 years prior to blood draw. (A) HIAP-2 gene expression in whole blood was not affected in MS relative to NS. (B) HIAP-2 gene expression is increased in PBMN cell RNA of RRA and SPMS patients relative to NS. (C) The increased HIAP-2 expression in PBMN cells is most likely due to increased HIAP-2 T cell gene expression. HIAP-2 is increased in T cells of RRA and SPMS patients relative to NS. *p<0.05.
Figure 4:
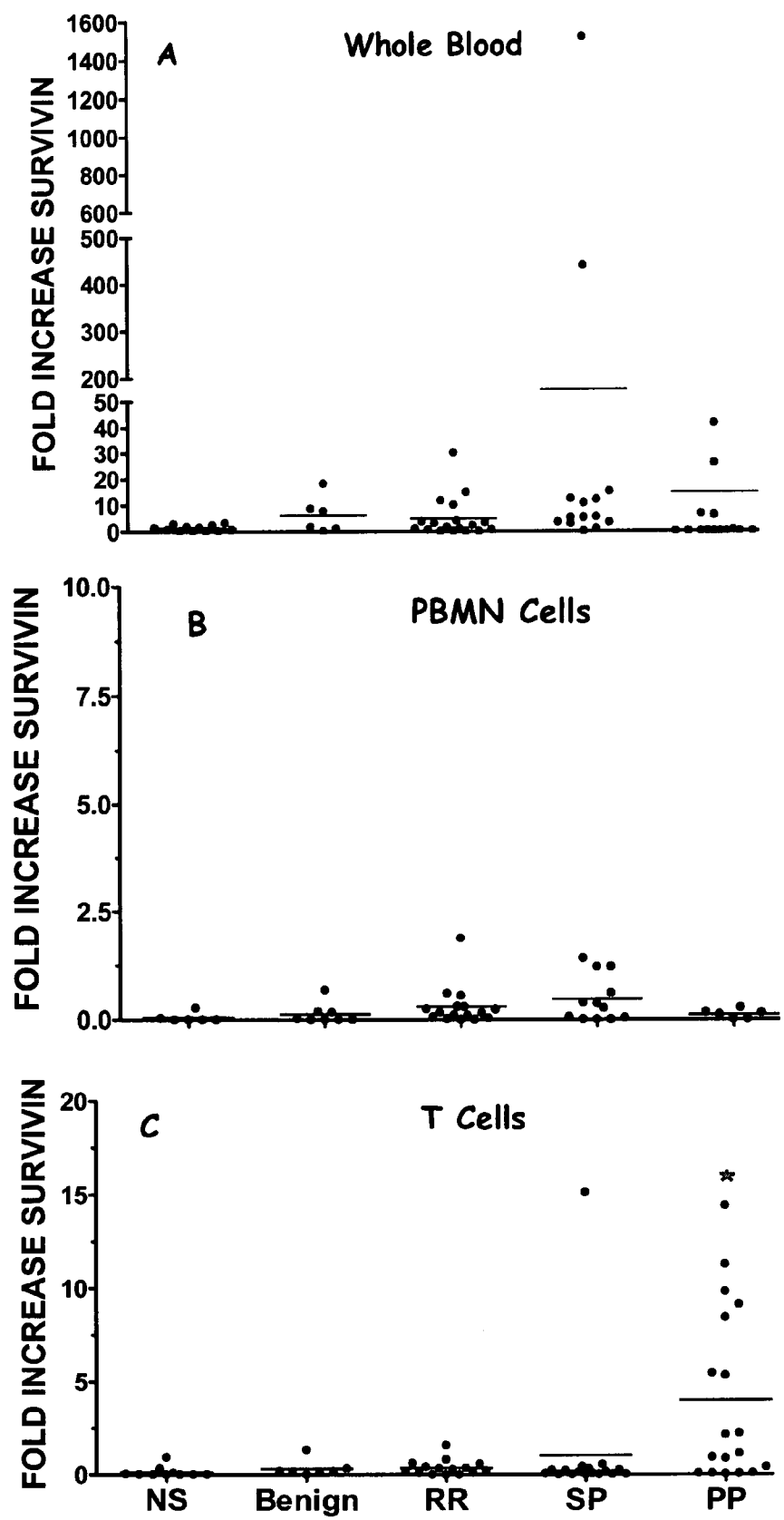
FIGS. 4A to 4C are graphs illustrating the relative quantification of survivin mRNA expression in RNA extracted from (A) whole blood, (B) PBMN cells and (C) T cells employing qRT-PCR. The graphs depict the expression of survivin mRNA relative to the expression of the endogenous control gene $\beta_2$ microglobulin ($2^{-\Delta\Delta CT}$) in normal subjects (NS) and patients with benign, Relapsing-Remitting (RR), Secondary-Progressive (SP) or Primary-Progressive (PP) MS patients. Quiescent (Q)=MS symptoms in remission at time of blood draw and the patient has not experienced any relapses in the 2 years prior to blood draw; Active (A)=MS symptoms are active at time of blood draw and the patient has experienced at least one relapse in the 2 years prior to blood draw. (A) Survivin gene expression in whole blood was not affected in MS relative to NS. (B) Survivin gene expression was not affected in PBMN cells of MS patients relative to NS. (C) Survivin gene expression was increased in T cells of patients with PPMS relative to NS and all other MS groups.
Figure 7:
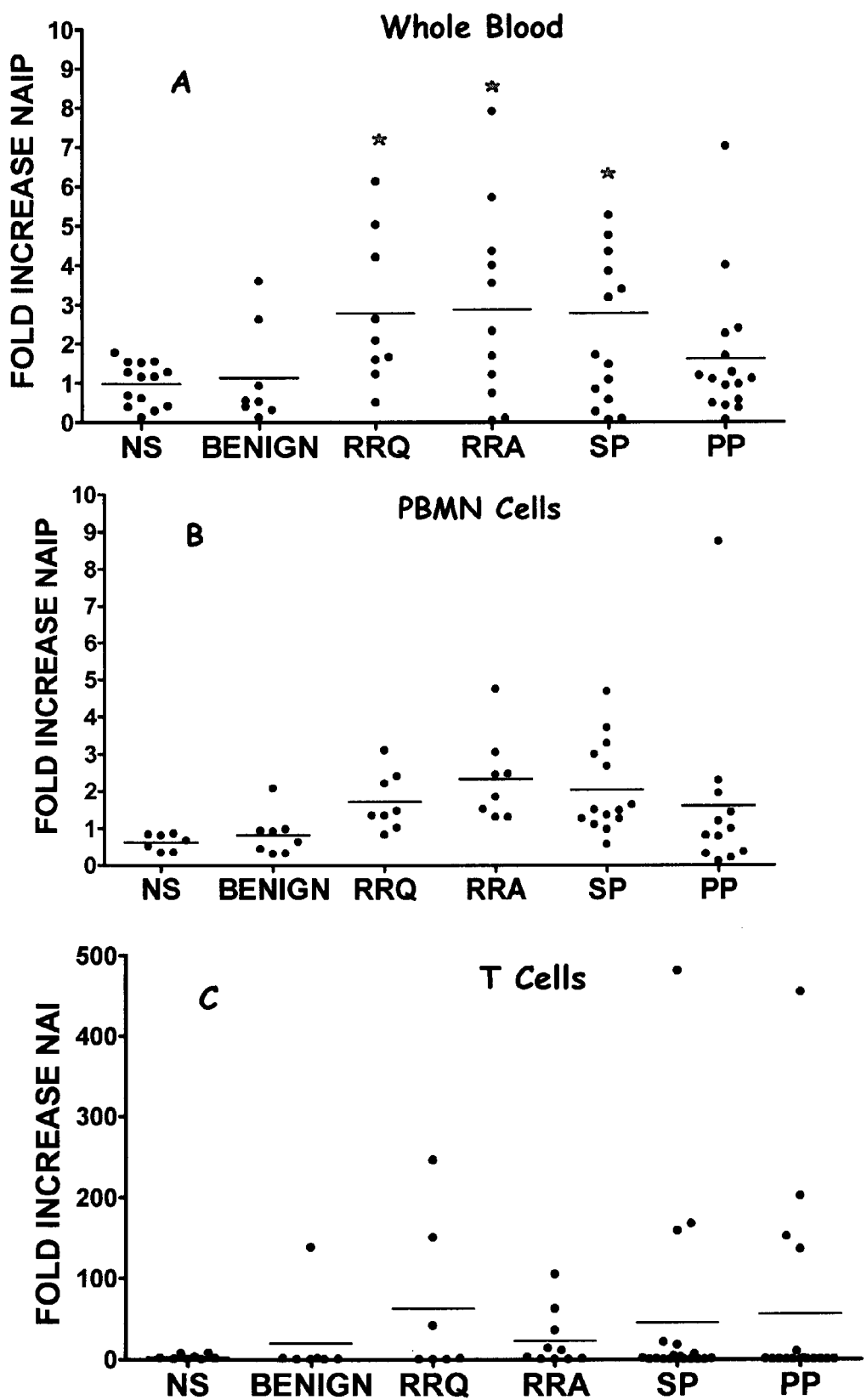
FIGS. 7A to 7C illustrates the relative quantification of NAIP mRNA expression in RNA extracted from (A) whole blood, (B) PBMN cells and (C) T cells employing qRT-PCR. This graph depicts the expression of NAIP mRNA relative to the expression of the endogenous control gene $\beta_2$ microglobulin ($2^{-\Delta\Delta CT}$) in normal subjects (NS) and patients with benign, Relapsing-Remitting (RR), Secondary-Progressive (SP) or Primary-Progressive (PP) MS patients. Quiescent (Q)=MS symptoms in remission at time of blood draw and the patient has not experienced any relapses in the 2 years prior to blood draw; Active (A)=MS symptoms are active at time of blood draw and the patient has experienced at least one relapse in the 2 years prior to blood draw. (A) NAIP gene expression in whole blood was increased in RRQ, RRA and SPMS relative to normal subjects. (B) NAIP gene expression was not affected in PBMN cells of MS patients relative to normal control subjects. (C) NAIP gene expression appeared to be increased in a subset of PPMS patients relative to normal control subjects (P>0.05).

XIAP mRNA expression was increased approximately four and a half-fold in PBMN cells from patients with RRA (n=10) or SPMS (n=16) compared to NS (n=11), or patients with benign MS (n=8), RRQ (n=10) or PPMS (n=12) [$F (5, 61)=4.180$, $p<0.01$]. There were no difference in PBMN cell XIAP expression between NS or patients with Benign, RRQ or PPMS (FIG. 1B). HIAP-1 expression in PBMN cells was similar in NS (n=8) as well as in patients with Benign (n=10), RR (n=16), SP (n=16) and PPMS (n=12) [$F (4,57)=1.605$, $p=0.186$] (FIG. 2B). HIAP-2 expression was increased approximately two-fold in PBMN cells from RRA (n=8) and SPMS patients (n=14) compared to NS (n=10), and patients with benign (n=9) MS [$F (5,57)=5.083$, $p<0.001$]. There were no differences in HIAP-2 PBMN mRNA levels among RRQ (n=9) or PPMS (n=12) patients (FIG. 3B). There was a weak positive correlation ($r=0.310$, $p<0.05$) between EDSS scores and HIAP-2 mRNA levels in PBMN cells. Survivin PBMN cell mRNA levels were the same in NS (n=6), patients with Benign (n=8), RR (n=16), SP (n=12), and PPMS (n=6) [$F (4,47)=1.655$, $p=0.178$] (FIG. 4B). NAIP expression in PBMN cells was similar in normal control subjects (n=7), or patients with Benign MS patients (n=10), qRRMS quiescent (n=7), aRRMS (n=8), SPMS (n=14) or PPMS patients (n=9) [$F (5,50)<1$, $p=0.545$], (FIG. 7B).

C. Resting T Cells

XIAP mRNA expression in resting T cells was similar in NS (n=13) and patients with Benign (n=10), RR (n=17), SP (n=20) and PPMS (n=17) [$F (4,72)=1.433$, $p=0.232$] (FIG. 1C). In contrast, HIAP-1 mRNA expression was elevated approximately three-fold in resting T cells from patients with RRMS irrespective of disease activity (n=19) compared to NS (n=11) and patients with benign or PPMS [$F (4,77)=3.871$, $p<0.01$] (FIG. 2C). There were no differences in T cell HIAP-1 mRNA levels between patients with RRMS and SPMS (n=22) (see FIG. 2C). In patients with RR (n=24) and SPMS (n=20) HIAP-2 mRNA expression was increased approximately two and a half-fold compared to NS (n=12) [$F (4,81)=2.528$, $p<0.01$]. There were no differences in T cell HIAP-2 mRNA expression between patients with benign MS (n=12) or PPMS (n=19) (FIG. 3C). Survivin T cell mRNA expression was increased almost four and a half fold in PPMS (n=18) relative to NS (n=10), patients with benign (n=7), RR (n=15) and SPMS (n=17) [$F (4,62)=4.271$, $p<0.01$]. There was a positive correlation ($r=0.376$; $p<0.05$) between the degree of disability as reflected by EDSS scores and survivin mRNA expression in T cells, (FIG. 4C). NAIP was also differentially increased in resting T cells of a small subset of PPMS patients. At this juncture, however, it is not clear what the increase in NAIP represents.

Table 3 summarizes the relationships between IAP expression patterns, immune cell subtype and multiple sclerosis subtype. The arrows (↑) indicate an increase in the IAP expression relative to control subjects.

TABLE 3

| MS Subtype | Whole blood | PBMN cells | Resting T cells |
|---|---|---|---|
| Benign | No change | No change | No change |
| RRMSQ | ↑ NAIP | No change | ↑ HIAP-1 |
| RRMSA | ↑ NAIP | ↑ XIAP, ↑ HIAP-2 | ↑ HIAP-1, ↑ HIAP-2 |
| SPMS | ↑ NAIP | ↑ XIAP, ↑ HIAP-2 | ↑ HIAP-2 |
| PPMS | No change | No change | ↑ Survivin |

Expression patterns of the IAPs in whole blood, PBMNs and T cells distinguish subtypes of MS. IAPs were not elevated in patients with benign MS. Patients with RRMS, RRMS or SPMS displayed elevated levels of NAIP in whole blood. Patients with relapse remitting MS that were quiescent (RRMSQ) displayed elevated HIAP-1 in resting T cells. By contrast, patients with relapse remitting MS that were in the active state (RRMSA) displayed elevated XIAP and HIAP-2 in PBMNs and elevated HIAP-1 and HIAP-2 in resting T cells. The same changes occurred in patients with secondary progressive MS (SPMS) with the exception that only HIAP-2 was elevated in resting T cells. Lastly, patients with primary progressive MS (PPMS) only displayed elevated survivin expression in resting T cells. Survivin up-regulation is often observed in many forms of cancer suggestive of increased resistance to apoptosis and elevated high proliferative status.

Western Blotting

Figure 5:
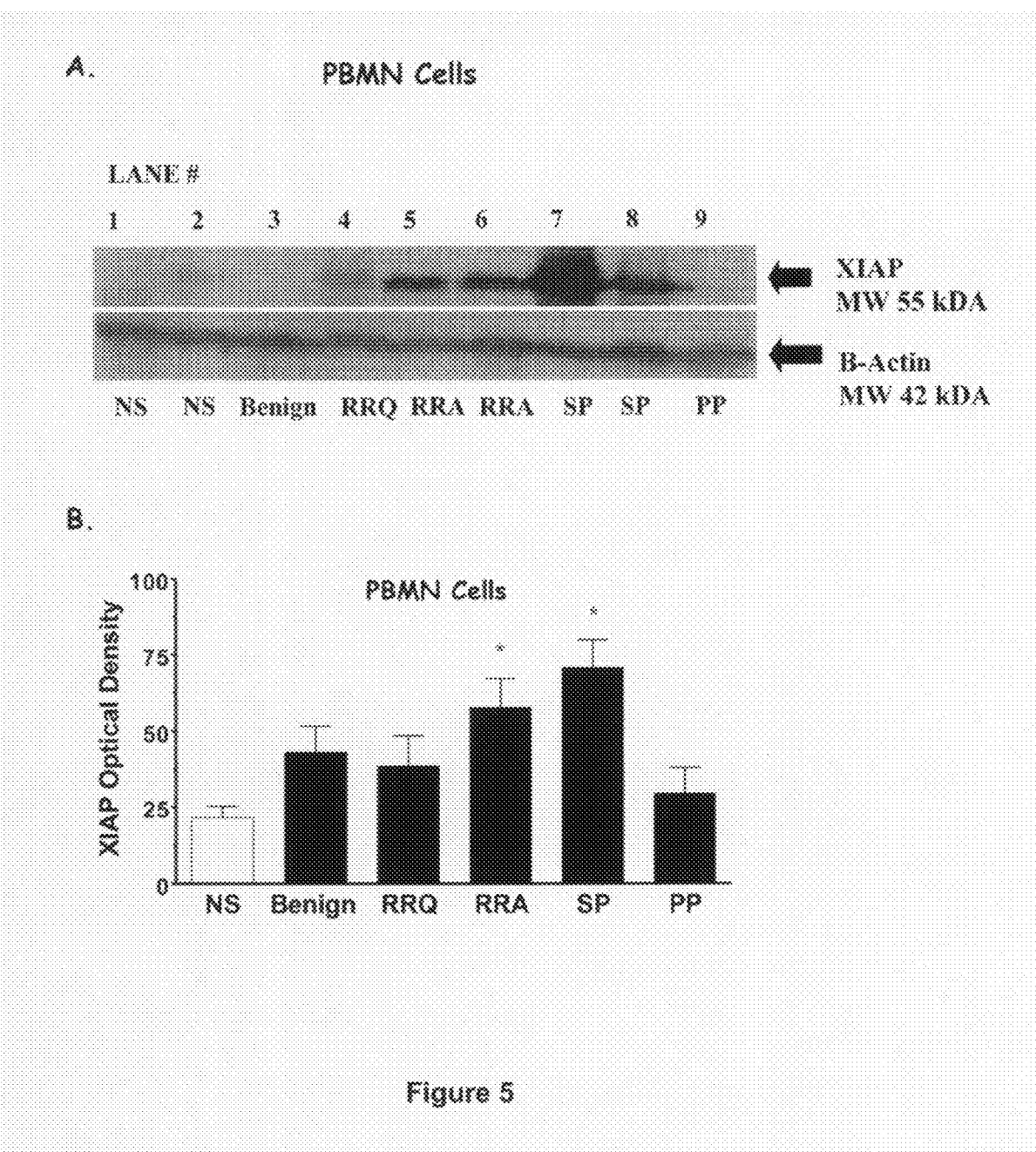
FIGS. 5A and 5B illustrate the IAP protein levels in patients with different types of MS and normal control subjects. A. XIAP protein levels in patients with different types of MS and normal control subjects. In PBMN cells there was a difference in XIAP protein levels between the various groups with increased levels of protein detected in RRA and SP MS patients relative to all other groups. These findings were matched by a concordant increase in XIAP PBMN cell mRNA levels in patients with RRA and SP MS relative to all other groups (see FIG. 1B). B. Optical density analysis confirmed the increase of XIAP protein in patients with RRA and SPMS (*p<0.05).
Figure 6:
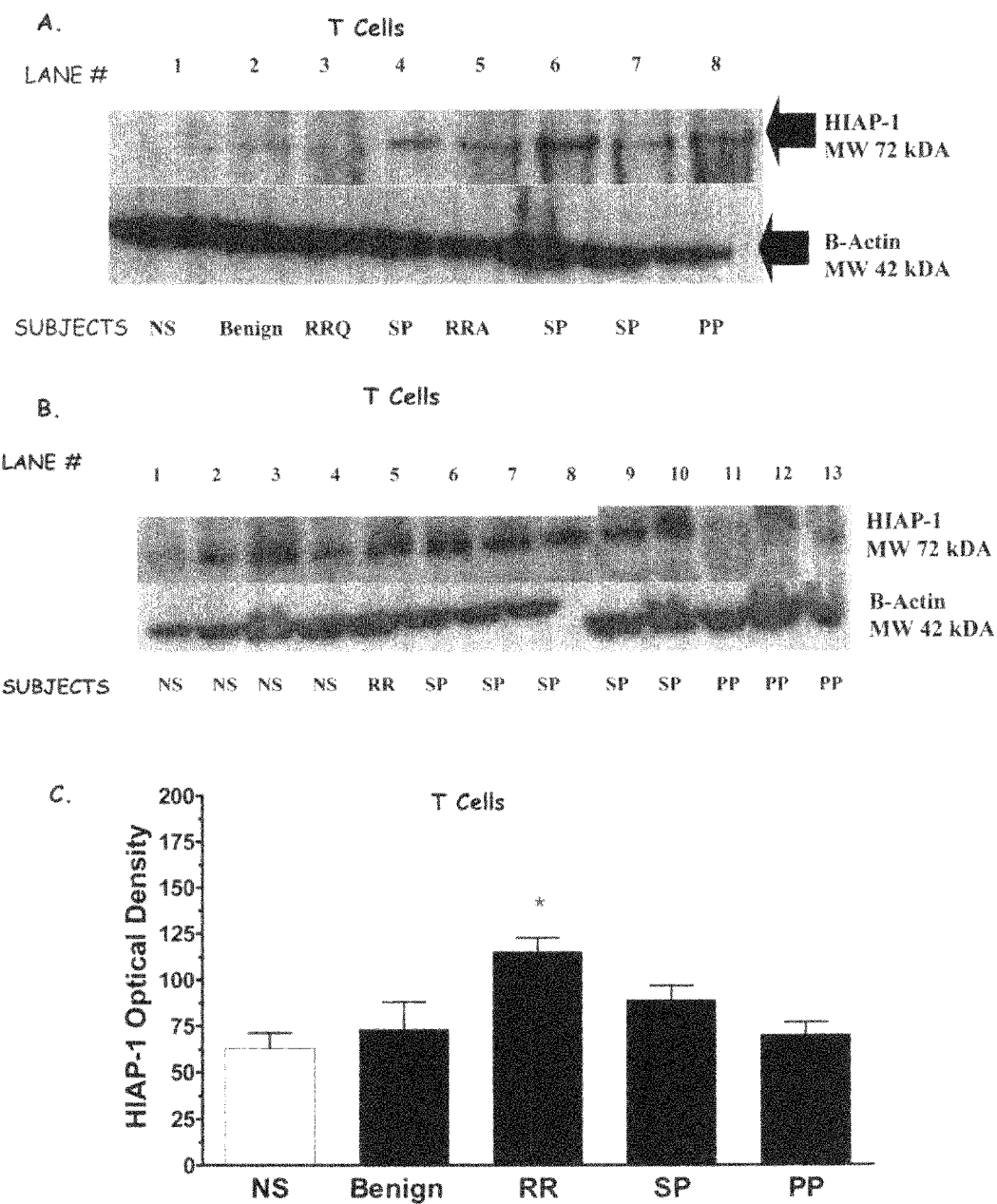
FIGS. 6A to 6C illustrate the HIAP-1 protein levels in patients with different types of MS and normal control subjects. (A) HIAP-1 protein levels in T cells from patients with RR, SP and PP MS appeared to be increased relative to subjects with benign MS and normal control subjects. (B) The variability of HIAP-1 protein expression in PPMS patients was reminiscent of the changes observed in mRNA (see FIG. 2C). (C) Optical density analysis confirmed the increase of HIAP-1 in RRMS relative to normal subjects, benign patients and patients with either SPMS or PPMS (*p<0.05).

XIAP PBMN cell optical density (55 kDa band) was increased approximately two and a half-fold in PBMN cells from patients with RRA (n=12) or SPMS (n=15) compared to NS (n=13), or patients with PPMS (n=10) [$F (5,65)=5.207$, $p<0.001$]. There were no differences in PBMN cell XIAP expression between NS or patients with Benign, RRQ or PPMS (FIG. 5). Quantification of the HIAP-1 band (72 kDa)

revealed a 1.5 fold elevation of this protein from extracts from T cells of patients with RRMS irrespective of disease activity (combined RRQ and RRA) relative to other groups [$F_{94, 56}$=6.144, $p<0.001$] (FIG. 6). The results obtained by western blotting were therefore consistent with those obtained by qRT-PCR.

Discussion

The present invention demonstrates that distinct patterns of elevated IAP expression (XIAP, HIAP-1, HIAP-2, survivin) in PBMN cells and resting T cells are associated with different types of MS. This finding is consistent with the proposal that MS is not a single clinical entity but rather a heterogeneous disorder. Our findings suggest that distinct apoptotic mechanisms are activated in different populations of immune cells in patients with various forms of MS. Furthermore, our results are consistent with the hypothesis that increased IAP expression may contribute to the pathogenesis of MS by delaying the removal of auto-reactive immune cells by apoptosis [Sharief and Semra 2001; Semra et al. 2002] thereby preventing the death of myelin-reactive immune cells resulting in inflammation and demyelination in the brain and spinal cord.

In the present investigation, XIAP mRNA and protein was differentially increased in PBMN cell fractions with no notable differences among groups of MS patients in whole blood or T cells. Increased PBMN cell expression of XIAP was noted in RRMS patients with a more active disease course as well as among patients with SPMS. Monocytes comprise about 3-8% of the leukocytes in the blood. It is therefore tempting to speculate that monocytes contribute to the elevation of XIAP mRNA and protein observed in patients with aggressive forms of MS. XIAP is expressed in normal monocytes but relatively undetectable in granulocytes. Moreover, exaggerated monocyte XIAP expression is associated with acute myeloid leukemia that has a poor clinical outcome [Tamm et al. 2000]. Neutrophils are the primary immune cell subtype in whole blood comprising up to approximately 70% of leukocytes present in whole blood. Neutrophils can regulate suppressor T cell responses to myelin [Zehntner et al. 2005b], have been associated with demyelinated plaques in a mouse model of experimental autoimmune encephalomyelitis [Tsunoda et al. 2000] and promote demyelination [Gaupp et al. 2003]. Calpain-mediated degradation of XIAP is though to play a critical role in controlling the number of circulating neutrophils [Kobayashi et al. 2002] while the ability of the bacterium *Anaplasma phagoctophilium* to delay neutrophil apoptosis is associated with reduced degradation of XIAP [Ge and Rikihisa 2006]. XIAP was not increased in whole blood of MS patients relative to normal control subjects although several patients with benign, RR, SP and PP MS demonstrated values that were greater than controls. These results suggest that at least as far as XIAP, HIAP-1 and HIAP-2 are concerned; the resistance of neutrophils to apoptosis does not play a major role in MS. The relative lack of XIAP mRNA induction in whole blood was not due to an overall decrease in T cell numbers or a reduced percentage of T cells in whole blood in MS patients as levels of XIAP mRNA in subsequent resting T cell fractions from the same patients were unremarkable. The lack of increased XIAP mRNA expression in T cells in patients with aggressive forms of MS contrasts with the report by Sharief and Semra [2001] in which elevated XIAP protein levels were observed in mitogen activated T cells isolated from RRMS patients relative to normal and neurological control subjects. One explanation for this discrepancy between the results of the present study and those of Sharief and Semra [2001] is that we examined levels of XIAP mRNA in resting T cells while levels of XIAP protein in mitogen activated T cells were examined in the former. In MS, T cells may be primed by PHA stimulation resulting in elevated XIAP expression.

The increase in XIAP, HIAP-1 and HIAP-2 in mitogen activated immune cells [Sharief et al. 2002b], while supporting a role for impaired activation-induced apoptosis in the immune cells of MS patients, may simply be an exaggeration of the immune cells sensitized to myelin antigens and thus more likely to display elevated IAP levels upon stimulation with PHA. Consistent with this notion, our inability to detect elevated XIAP levels in resting T cells from MS patients suggests that mitogen stimulation artificially activates a survival pathway by mechanisms not relevant to MS. In further support of this hypothesis, mitogen-stimulated apoptosis in non-myelin reactive CD4+ and CD8+ T cells has been reported to be comparable in MS patients and normal control subjects while activation of myelin-reactive CD4+ and CD8+ T cells was associated with decreased Fas associated apoptosis in MS patients [Saresella et al. 2005; Zang et al. 1999]. The demonstration that XIAP is increased in resting PBMN cells in the present study suggests that these cells have been stimulated with MS relevant antigens in the peripheral blood circulation such as myelin basic protein or myelin oligodendrocyte glycoprotein, inducing differentiation and prolonging their lifespan. Although monocytes, B lymphocytes and T lymphocytes compose the cell types present in the PBMN cell fraction, the increase in XIAP expression was not present in T cell fractions, thus implicating either B lymphocytes or monocytes as the major contributor to increases in this apoptotic gene. While evidence for increased XIAP levels in B lymphocytes in MS is lacking, the contribution of XIAP expression in B lymphocytes to the overall increase in PBMN cell XIAP in patients with RRMS and SPMS cannot be dismissed entirely. In humans XIAP, HIAP-1 and HIAP-2 mRNAs are strongly expressed in B lymphocytes of normal subjects as well as in patients with B-cell chronic lymphocytic leukemia as measured by RNAse protection assay [Munzert et al. 2002]. Still, monocytes have an important role in the pathogenesis of MS and are one of the primary cell types responsible for tissue damage [van der Goes et al. 2005]. Yet, it has previously been demonstrated in monocytes derived from normal subjects that differentiation induction and clonal expansion led to an upregulation of XIAP protein, an effect not observed in neutrophils, contributing to increased longevity of cells derived from the monocyte lineage while treatment with XIAP antisense oligonucleotides resulted in significant loss of cell viability [Miranda et al. 2003]. XIAP, HIAP-1 and HIAP-2 mRNA is expressed in neutrophils albeit the relative protein expression is low. Yet stimulation of neutrophils with lipopolysaccharide (LPS) of gram-negative bacteria induces upregulation of HIAP-1 and HIAP-2 mRNA. Moreover, in septic patients characterized by infection of the bloodstream by toxin-producing bacteria, delayed neutrophil apoptosis has been associated with increased XIAP mRNA expression with no changes observed in HIAP-1 or HIAP-2 mRNA expression in patients possibly contributing to the persistence of an inflammatory reaction [O'Neill et al. 2004]. The lack of XIAP, HIAP-1 and HIAP-2 in neutrophils of MS patients relative to mitogen-induced IAP and reduced neutrophil apoptosis in septic patients demonstrates the diversity of the immune cells involved in differential immune perturbations and outlines the specificity of inflammatory events underlying MS pathology. Taken together, while neutrophils may characterize more acute peripheral inflammatory conditions, increased expression of monocytes displaying exaggerated XIAP mRNA levels suggest that these cell types play a major role in more aggressive types of MS, characterized by widespread tissue damage and marked neurological disability.

Expression of HIAP-1 and HIAP-2 appear to be more tissue specific than XIAP [Liston et al. 2003; Vischioni et al. 2006]. Highest levels of HIAP-1 and HIAP-2 are found in tissues of lymphoid origin including the thymus, peripheral lymphocytes and spleen [Vischioni et al. 2006]. Both HIAP-1 and HIAP-2 have CARD domains and are involved in the inactivation of caspase 9 [Reed et al. 2003]. Through homotypic protein-protein interactions CARD domains are thought to influence function of inflammatory and apoptotic signaling pathways [Reed et al. 2003]. HIAP-1 and HIAP-2 mRNA is increased in T cells in MS patients that are experiencing relapses/remissions and/or disease progression, respectively suggesting a prominent role for inflammatory T cells in the pathogenesis of RRMS disease progression reminiscent of data previously reported by Sharief et al. in mitogen stimulated T cells. Moreover, it has been revealed that the phenotypic profile of immune cell types differs in patients in early MS at least as far as in patients that have experienced a clinically isolated syndrome. Patients with active MRI activity in the proceeding year displayed distinct changes in peripheral lymphocyte subsets relative to MRI-inactive patients that were predictive of MRI activity in early disease. Interestingly, it has been reported that infiltrating and clonally expanded autoreactive T cells persisted for longer than 7 years in the CSF and blood of patients with RRMS, irrespective of interferon-β (IFN-β) treatment history, which does not eliminate autoreactive T cells, contributing to the propensity of increased clinical exacerbations and possibly the eventual progression of neural disability [Skulina et al. 2004]. While clonal expansion of auto-reactive T cells have been identified in the blood and CSF of normal subjects, these cell populations are susceptible to apoptosis [Skulina et al. 2004], while myelin-primed T cells in MS are resistant to programmed cell death proliferating and inducing CNS damage [Pender 1998]. In the present investigation, increased expression of the anti-apoptotic genes HIAP-1 and HIAP-2 in RRMS and SPMS would render the cells apoptosis-resistant, increasing their life-span and contributing to myelin destruction at the very least during the relapse phase. The sole increase in HIAP-1 mRNA levels in un-stimulated T cells is consistent with a critical role for this population of immune cells in MS. The differential expression of IAPs suggests cell-type specific apoptotic pathways and redundancy in the immune system such that defects in one pathway will not abolish apoptosis altogether.

The gene expression pattern of HIAP-2 within immune cells isolated from MS patients differed slightly from the pattern of expression observed for HIAP-1. Elevated PBMN cell HIAP-2 expression was found in patients with RRA and SPMS likely reflecting a contribution from T cells. HIAP-2 expression was increased in T cells in patients with RRA and SPMS, but not subjects with benign or PPMS, suggesting that the increased expression of this anti-apoptotic gene in T cells is associated with a clinical course characterized by either relapses and remission or an unrelenting disease progression. Benign MS patients can convert to RRA and SPMS with time, and increased IAP levels within specific immune cell populations may have prognostic value indicative of a change in MS disease course prior to the reappearance of symptoms. In summary, XIAP, HIAP-1 and HIAP-2 displayed cell specific induction patterns among patients with different subtypes and severity of RRMS that may perpetuate the continuous phasic presentation of inflammation and resolution within the CNS.

Survivin is a unique member of the IAP family implicated in both cell proliferation and apoptosis [Ambrosini et al. 1997]. The survivin pathway interfaces with both the cell-death machinery and mechanisms of cell-cycle progression and microtubule stability, specifically expressed during the G2/M phase of the cell cycle. Survivin expression is undetectable in most normal adult tissues [Fukuda and Pelus 2001] including PBMN cells, T cells and whole-blood cell lysates, but is over expressed in virtually every human tumor that has been studied [Ouhtit 2007]. Survivin expression was relatively undetectable in whole blood, PBMN cells or resting T lymphocytes in NS and patients with benign, RR and SPMS, reminiscent of the findings of Sharief and Semra [Livak and Schmittgen 2001]. Although several RRMS and SPMS patients with elevated EDSS scores demonstrated increased survivin levels in whole blood and PBMN cells suggestive of active inflammatory disease these increases were not associated with a specific MS disease subtype. It should be mentioned that although survivin mRNA levels were low or undetectable in most normal and benign MS blood samples, detectable levels of survivin expression have been previously reported in normal peripheral lymphocytes [Shinozawa et al. 2000] that are upregulated during clonal expansion of these cells as well as non-malignant T cells increasing their resistance to apoptosis [Sharief and Semra 2001]. In comparison, mitogen activation of T cells in culture elevated survivin expression may be associated with clonal expansion as reported by Sharief and Semra [Sharief et al. 2002a] and therefore may simply reflect cell proliferation and not apoptotic status. Survivin expression prior to T cell activation was undetectable, while increased survivin expression was found in memory T cells following stimulation with PHA in lymphocytes isolated from normal donors [Kornacker et al. 2001]. Indeed, survivin is now believed to regulate chromosome segregation during mitosis [Fukuda and Pelus 2001]. In the present study, the scattered increase in survivin expression in whole-blood and PBMN cells may be indicative of cells undergoing division and proliferation at the time of blood draw, although the correlation of survivin levels with EDSS disability may be of pathogenic significance in MS, at the very least allowing prolonged immune cell viability, proliferation and ultimately contributing to CNS damage and clinical disability.

It should be underscored; however, that in the present study, PPMS patients displayed survivin levels approximately 5 fold higher in resting T cells relative to NS, benign, RR and SPMS. Primary progressive MS has been associated with a specific polymorphism of the cytotoxic T-lymphocyte antigen 4 gene, that down-regulates T-cell function [Maurer et al. 2002]. In contrast, a small portion of T cells with elevated survivin would be expected to reduce T-cell elimination producing a more prolonged disease time-course. It is notable that survivin, a marker and potential target for the treatment of cancer therapy is upregulated in a type of MS for which there is no effective treatment As a result, survivin may hold diagnostic utility for distinguishing SPMS and PPMS in patients for which a clear clinical history is unavailable.

Neuronal apoptosis inhibitory protein (NAIP) like XIAP, human IAP-1 (HIAP-1) and human IAP-2 (HIAP-2) possesses 3 BIR domains, while survivin possesses 1 BIR domain, that support the suppression of caspase 3 and 7; the two most potent effector caspases NAIP, unlike the other IAPs, has a NACHT domain and proteins of the NACHT family may serve as critical pathogen sensing and signal transducing molecules within the innate immune system. In contrast to XIAP, HIAP-1, or HIAP-2 expression in whole blood, NAIP mRNA expression (FIG. 7A) was increased approximately two to three-fold elevation of NAIP mRNA in the whole blood from patients with qRRMS (n=9), aRRMS (n=11), SPMS (n=14), PPMS (n=8) relative to patients with Benign MS (n=8) or healthy subjects (n=14) [F (5, 59)=1.947, p=0.1]. There was a moderate positive correlation (r=0.368, p<0.01) between EDSS disability and NAIP mRNA expression in whole blood. There were no difference between whole blood NAIP expression between normal subjects (n=14) or patients with Benign MS (n=8). Neutrophils are the primary immune cell subtype in the PBMN fraction that comprise up to approximately 70% of leukocytes present in whole blood. Neutrophils can regulate suppressor T cell responses to myelin, have been associated with demyelinated plaques in a mouse model of experimental autoimmune encephalomyelitis and promote demyelination. Calpain-mediated degradation of XIAP is though to play a critical role in controlling the number of circulating neutrophils while the ability of the bacterium *Anaplasma phagoctophilium* to delay neutrophil apoptosis is associated with reduced degradation of XIAP. However, XIAP is not increased in whole blood.

One unexpected observation was the differential expression of NAIP within whole blood. Regarding NAIP expression in patients within the different sub-types of MS, NAIP was differentially increased, unlike the other IAPs in which the increase was restricted to a specific cell fraction, in both whole blood of patients with RRMS and SPMS. Interestingly, NAIP is increased in whole blood but not PBMN cell mRNA of patients with RR and SPMS. The difference in the expression of NAIP mRNA in whole blood compared to PBMN cell fractions likely reflects the increased number of granulocytes or dendritic cells in whole blood, cells in low levels or relatively absent in PBMN cell fractions. NAIP possess a NACHT NTPase domain that codes for proteins involved in intracellular pathogen sensing and regulation of the innate immune response and inflammation. It is of note that NACHT gene mutations have been associated with inflammatory bowel disease, suggesting a prominent role of NACHT proteins in deterring pathogens from the gut. The NACHT domain is also present in those proteins involved in Major Histocompatability Complex (MHC) type II antigen transcription. MHC II antigens are present on dendritic cells, macrophages and neutrophils, the major antigen presenting cells (APC) involved in the innate immune response, representing the initial line of defense against foreign pathogens, present in whole blood. In RR and SP MS patients experiencing relapses, NAIP may increase the lifespan of APC such as neutrophils. Gene and protein expression of HIAP-1, HIAP-2 and XIAP are found in neutrophils, although at relatively low levels compared to NAIP and survivin. Monocytes in whole blood can differentiate into phagocytotic macrophages or dendritic cells (DCs). DCs are antigen-presenting leukocytes that function to initiate the immune response by activating T-lymphocytes and stimulating the secretion of cytokines. In this regard, DCs stimulate an immune response that may be prolonged by the extended survival of DCs by blocking DC apoptosis. In normal subjects, less than 0.1% of circulating leukocytes are immature DCs. Mature DCs are localized in lymphoid tissues. However, among individuals with RR, SP and PP MS circulating dendritic cells secreting pro-inflammatory cytokines are increased relative to normal control subjects that are thought to reflect a prominent role of DCs in MS disease pathogenesis. Under basal states of inactivation, NAIP is strongly expressed in immature DCs, while HIAP-1, HIAP-2 are rather weakly expressed, and XIAP and survivin are not expressed at all. Upon activation with antigen and subsequent maturation, NAIP expression was down regulated while levels of XIAP, HIAP-1 and HIAP-2 gene expression increased. Survivin levels remained undetectable. Bcl-2 and Bcl-xL, members of the Bcl-2 family of anti-apoptotic genes, were not or rather weakly expressed, in DCs, respectively. Although Bcl-2 protein levels are high in resting T lymphocytes, the expression of Bcl-2 protein was similarly expressed in basal and cultured T cells activated with PHA among normal subjects and corresponding patients with RRMS. In humans, NAIP mRNA levels are low while XIAP, HIAP-1 and HIAP-2 mRNAs are strongly expressed in B lymphocytes of normal subjects. NAIP gene expression appears to be regulated by different factors than HIAP-1, HIAP-2, XIAP, survivin and the Bcl-2 family. The increase of NAIP expression in whole blood likely reflects increased survival of immune cells involved in inflammatory processes and myelin damage as reflected by increased EDSS scores.

In the mouse, NAIP is highly expressed in macrophages. NAIP is increased in macrophages in mice in response to infection with an intracellular pathogen (*Legionella pneumophila*) that causes Legionnaire's disease, an acute form of pneumonia, in humans. While the success of *Legionella pneumophila* infection is dependant upon macrophage apoptosis, inducible NAIP expression within macrophages serves a protective role by inhibiting caspase 3 activities thus increasing the lifespan of the cell. Monocytes, macrophages, neutrophils and dendritic cells secrete pro-inflammatory cytokines that are associated with the inflammatory relapse phase of relapsing-remitting forms of MS. It is not clear at this juncture whether the increase NAIP expression in sub-types of MS with a prominent inflammatory response dictates specific immune cell contributions to the heterogeneous sub-types of MS, defining inflammatory and non-inflammatory conditions. Yet, neutrophil apoptosis regulation during an immune-mediated inflammatory response plays a key role in its resolution. Neutrophils are activated following release of pro-inflammatory cytokines, including IL-1, IL-6, tumor necrosis factor $\alpha$ and interferon $\gamma$ that also serve to inhibit apoptotic death. Increase of NAIP in whole blood RNA from RR and SPMS patients, suggests that over expression of NAIP may prolong neutrophils-induced inflammatory response which may be the basis for the correlation of NAIP in whole blood with EDSS scores, akin to the response of macrophages to infection with *Legionella pneumophila* associated with the relapse phase of the disease underlying extensive myelin damage. Increased expression of NAIP in inflammatory neutrophils would prevent their apoptotic deletion and delay resolution of acute MS symptomatology.

CONCLUSIONS

Taken together, the present findings indicate that specific patterns of IAP expression in distinct populations of immune cells have potential diagnostic and prognostic value for MS. To recapitulate, high levels of XIAP and HIAP-2 expression in PBMN cells and HIAP-2 in T cells may be associated with aggressive forms of this disorder (RRA and SPMS) characterized by inflammation that are best managed through early intervention. In contrast, XIAP, HIAP-1 and HIAP-2 expression in immune cell subsets is not elevated in benign and primary progressive forms of MS that do not do not require treatment or do not respond to current disease modifying therapies, respectively. In patients with PPMS, elevated expression of survivin may provide a novel therapeutic target for this devastating form of MS in which there are no current treatments. In addition to the prognostic value of IAP expression within distinct cell populations, our findings suggest that apoptotic dysregulation of potentially autoreactive immune cells in MS occurs through multiple immune pathways involving cells of both the innate (PBMN cells) and the adaptive (T cells) immune systems. The over expression of IAPs increase the resistance of specific cell types to apoptosis that contribute to the various subtypes of MS. It is of note that pre-clinical studies with the XIAP anti-sense molecule (data not shown) demonstrate that decreasing levels of XIAP in the immune system reduce symptom severity in an animal model of MS [Zehntner et al. 2005a]. Preliminary studies in cancer patients suggest that this compound has clinical efficacy suggesting that such a compound may represent a novel treatment for other diseases where impaired apoptosis has been implicated such as MS. In conclusion, basal expression patterns of several IAPs in specific immune cell populations not only reflect the diverse range of apoptotic mechanisms involved in MS pathogenesis but may have diagnostic utility in distinguishing between various subtypes of MS and serve as potential drug targets for different forms of this autoimmune disorder.

LITERATURE CITED

Ambrosini G, Adida C, Altieri D C. A novel anti-apoptosis gene, survivin, expressed in cancer and lymphoma. Nature Medicine 1997; 3: 917-921.

Apoptosis induction as a therapeutic intervention to eliminate encephalitogenic T cells using antisense XIAP (AEG35169) in a murine model of EAE. 2005a. Boston, Mass., Abstract presented at the 5th Annual Meeting of the Federation of Clinical Immunology Societies. Ref Type: Conference Proceeding.

Bernard C C A, Derosbo N K. Multiple-Sclerosis—An Autoimmune-Disease of Multifactorial Etiology. Current Opinion in Immunology 1992; 4: 760-765.

Biswas P, Mantelli B, Sica A et al. Expression of CD4 on human peripheral blood neutrophils. Blood 2003; 101: 4452-4456.

Bruck W, Stadelmann C. Inflammation and degeneration in multiple sclerosis. Neurological Sciences 2003; 24: S265-S267.

Calabresi P A. Diagnosis and management of multiple sclerosis. American Family Physician 2004; 70: 1935-1944.

Chofflon M. Mechanisms of action for treatments in multiple sclerosis: Does a heterogeneous disease demand a multi-targeted therapeutic approach? BioDrugs. 2005; 19: 299-308.

Comi C, Leone M, Bonissoni S et al. Defective T cell Fas function in patients with multiple sclerosis. Neurology 2000; 55: 921-927.

Conze D B, Albert L, Ferrick D A et al. Posttranscriptional downregulation of c-IAP2 by the ubiquitin protein ligase c-IAP1 in vivo. Mol. Cell Biol. 2005; 25: 3348-3356.

Crocker S J, Wigle N, Liston P et al. NAIP protects the nigrostriatal dopamine pathway in an intrastriatal 6-OHDA rat model of Parkinson's disease. European Journal of Neuroscience. 2001; 14:391-400.

Damiano J S, Oliveira V, Welsh K et al. Heterotypic interactions among NACHT domains: implications for regulation of innate immune responses. Biochemical Journal. 2004; 381:213-219

Diez E, Yaraghi Z, MacKenzie A et al. The Neuronal Apoptosis Inhibitory Protein (Naip) Is Expressed in Macrophages and Is Modulated After Phagocytosis and During Intracellular Infection with *Legionella pneumophila*. J Immunol. 2000; 164:1470-1477

Eckelman B P, Salvesen G S. The human anti-apoptotic proteins cIAP1 and cIAP2 bind but do not inhibit caspases. Journal of Biological Chemistry 2006; 281: 3254-3260.

Fukuda S, Pelus L M. Regulation of the inhibitor-of-apoptosis family member survivin in normal cord blood and bone marrow CD34(+) cells by hematopoietic growth factors: implication of survivin expression in normal hematopoiesis. Blood 2001; 98: 2091-2100.

Gaupp S, Pitt D, Kuziel W A, Cannella B, Raine C S. Experimental autoimmune encephalomyelitis (EAE) in CCR2(−/−) mice: susceptibility in multiple strains. Am. J. Pathol. 2003; 162: 139-150.

Ge Y, Rikihisa Y. Anaplasma phagocytophilum delays spontaneous human neutrophil apoptosis by modulation of multiple apoptotic pathways. Cell Microbiol. 2006; 8: 1406-1416.

Hafler D A, Weiner H L. Ms—A Cns and Systemic Autoimmune-Disease. Immunology Today 1989; 10: 104-107.

Hawkins S A, McDonnell G V. Benign multiple sclerosis? Clinical course, long term follow up, and assessment of prognostic factors. Journal of Neurology Neurosurgery and Psychiatry 1999; 67: 148-152.

Holcik M, Gibson H, Komeluk R G. XIAP: Apoptotic brake and promising therapeutic target. Apoptosis 2001; 6: 253-261.

Kaur S, Wang F, Venkatraman M, Arsura M. X-linked inhibitor of apoptosis (XIAP) inhibits c-Jun N-terminal kinase 1 (JNK1) activation by transforming growth factor beta1 (TGF-beta1) through ubiquitin-mediated proteosomal degradation of the TGF-beta1-activated kinase 1 (TAK1). J. Biol. Chem. 2005; 280: 38599-38608.

Kobayashi S, Yamashita K, Takeoka T et al. Calpain-mediated X-linked inhibitor of apoptosis degradation in neutrophil apoptosis and its impairment in chronic neutrophilic leukemia. J. Biol. Chem. 2002; 277: 33968-33977.

Kornacker M, Verneris M R, Kornacker B, Scheffold C, Negrin R S. Survivin expression correlates with apoptosis resistance after lymphocyte activation and is found preferentially in memory T cells. Immunology Letters 2001; 76: 169-173.

Liston P, Fong W G, Korneluk R G. The inhibitors of apoptosis: there is more to life than Bcl2. Oncogene 2003; 22: 8568-8580.

Liston P, Roy N, Tamai K et al. Suppression of apoptosis in mammalian cells by NAIP and a related family of IAP genes. Nature. 1996; 379:349-353.

Livak K J, Schmittgen T D. Analysis of relative gene expression data using real-time quantitative PCR and the 2(-Delta Delta C(T)) Method. Methods 2001; 25: 402-408.

Mahoney J A, Rosen A. Apoptosis and autoimmunity. Current Opinion in Immunology 2005; 17: 583-588.

Maurer M, Loserth S, Kolb-Maurer A et al. A polymorphism in the human cytotoxic T-lymphocyte antigen 4 (CTLA4) gene (exon 1+49) alters T-cell activation. Immunogenetics 2002; 54: 1-8.

McDonald W I, Compston A, Edan G et al. Recommended diagnostic criteria for multiple sclerosis: Guidelines from the International Panel on the Diagnosis of Multiple Sclerosis. Annals of Neurology 2001; 50: 121-127.

McDonnell G V, Cabrera-Gomez J, Calne D B, Li D K B, Oger J. Clinical presentation of primary progressive multiple sclerosis 10 years after the incidental finding of typical magnetic resonance imaging brain lesions—The subclinical stage of primary progressive multiple sclerosis may last 10 years. Multiple Sclerosis 2003; 9: 204-209.

McDonnell G V, Hawkins S A. Primary progressive multiple sclerosis: increasing clarity but many unanswered questions. Journal of the Neurological Sciences 2002; 199: 1-15.

Miranda M B, Dyer K F, Grandis J R, Johnson D E. Differential activation of apoptosis regulatory pathways during monocytic vs granulocytic differentiation: a requirement for Bcl-X-L and XIAP in the prolonged survival of monocytic cells. Leukemia 2003; 17: 390-400.

Munzert G, Kirchner D, Stobbe H et al. Tumor necrosis factor receptor-associated factor 1 gene overexpression in B-cell chronic lymphocytic leukemia: analysis of NF-kappa B/Rel-regulated inhibitors of apoptosis. Blood 2002; 100: 3749-3756.

Nachmias B, Ashhab Y, Ben Yehuda D. The inhibitor of apoptosis protein family (IAPs): an emerging therapeutic target in cancer. Seminars in Cancer Biology 2004; 14: 231-243.

Noseworthy J H, Lucchinetti C, Rodriguez M, Weinshenker B G. Medical progress: Multiple sclerosis. New England Journal of Medicine 2000; 343: 938-952.

O'Neill A J, Doyle B T, Molloy E et al. Gene expression profile of inflammatory neutrophils: Alterations in the inhibitors of apoptosis proteins during spontaneous and delayed apoptosis. Shock 2004; 21: 512-518.

Ouhtit, A. Matrougui K. Bengrine A. Koochekpour S. Zerfaoui M. Yousief Z. Survivin is not only a death encounter but also a survival protein for invading tumor cells. Front Biosci. 1(12), 1260-1270. 2007. Ref Type: Journal (Full).

Pari G, Berrada F, Verge G et al. Immunolocalization of NAIP in the human brain and spinal cord. Neuroreport. 2000; 11:9-14.

Pender M P. Genetically determined failure of activation-induced apoptosis of autoreactive T cells as a cause of multiple sclerosis. Lancet 1998; 351: 978-981.

Pender M P, Rist M J. Apoptosis of inflammatory cells in immune control of the nervous system: Role of glia. Glia 2001; 36: 137-144.

Pittock S J, Mayr W T, McClelland R L et al. Disability profile of MS did not change over 10 years in a population-based prevalence cohort. Neurology 2004; 62: 601-606.

Polman C H, Reingold S C, Edan G et al. Diagnostic criteria for multiple sclerosis: 2005 Revisions to the "McDonald Criteria". Annals of Neurology 2005; 58: 840-846.

Reed J C, Doctor K, Rojas A et al. Comparative analysis of apoptosis and inflammation genes of mice and humans. Genome Research 2003; 13: 1376-1388.

Rinaldi L, Gallo P, Calabrese M et al. Longitudinal analysis of immune cell phenotypes in early stage multiple sclerosis: distinctive patterns characterize MRI-active patients. Brain 2006; 129: 1993-2007.

Robertson G S, Crocker S J, Nicholson D W, Schulz J B. Neuroprotection by the inhibition of apoptosis. Brain Pathology 2000; 10: 283-292.

Roy N, Mahadevan M S, McLean M et al. The Gene for Neuronal Apoptosis Inhibitory Protein Is Partially Deleted in Individuals with Spinal Muscular-Atrophy. Cell. 1995; 80:167-178.

Salvesen G S, Duckett C S. IAP proteins: Blocking the road to death's door. Nature Reviews Molecular Cell Biology 2002; 3: 401-410.

Saresella M, Marventano I, Speciale L et al. Programmed cell death of myelin basic protein-specific T lymphocytes is reduced in patients with acute multiple sclerosis. Journal of Neuroimmunology 2005; 166: 173-179.

Segal B M, Cross A H. Fas(t) track to apoptosis in MS—TNF receptors may suppress or potentiate CNS demyelination. Neurology 2000; 55: 906-907.

Seki H, Tsukamoto T, Aso H, Tamura K. Intrathecal Synthesis of Immunosuppressive Acidic Protein (Iap) in Patients with Multiple-Sclerosis and Other Inflammatory Neurological Diseases. Journal of the Neurological Sciences 1988; 85: 259-266.

Semra Y K, Seidi O A, Sharief M K. Disease activity in multiple sclerosis correlates with T lymphocyte expression of the inhibitor of apoptosis proteins. Journal of Neuroimmunology 2002; 122: 159-166.

Sharief M K, Noori M A, Douglas M R, Semra Y K. Upregulated survivin expression in activated T lymphocytes correlates with disease activity in multiple sclerosis. European Journal of Neurology 2002a; 9: 503-510.

Sharief M K, Noori M A, Zoukos Y. Reduced expression of the inhibitor of apoptosis proteins in T cells from patients with multiple sclerosis following interferon-beta therapy. Journal of Neuroimmunology 2002b; 129: 224-231.

Sharief M K, Semra Y K. Upregulation of the inhibitor of apoptosis proteins in activated T lymphocytes from patients with multiple sclerosis. Journal of Neuroimmunology 2001; 119: 350-357.

Shinozawa I, Inokuchi K, Wakabayashi I, Dan K. Disturbed expression of the anti-apoptosis gene, Survivin, and EPR-1 in hematological malignancies. Leukemia Research 2000; 24: 965-970.

Siva A. The spectrum of multiple sclerosis and treatment decisions. Clinical Neurology and Neurosurgery 2006; 108: 333-338.

Skulina C, Schmidt S, Dornmair K et al. Multiple sclerosis: Brain-infiltrating CD8(+) T cells persist as clonal expansions in the cerebrospinal fluid and blood. Proceedings of the National Academy of Sciences of the United States of America 2004; 101: 2428-2433.

Stroncek D F, Clay M E, Smith J, Jaszcz W B, Herr G, McCullough J. Comparison of two blood cell separators in collecting peripheral blood stem cell components. Transfusion Medicine 1997; 7: 95-99.

Tamm I, Kornblau S M, Segall H et al. Expression and prognostic significance of IAP-family genes in human cancers and myeloid leukemias. Clinical Cancer Research 2000; 6: 1796-1803.

Todaro M, Zeuner A, Stassi G. Role of apoptosis in autoimmunity. Journal of Clinical Immunology 2004; 24: 1-11.

Traugott U, Reinherz E L, Raine C S. Multiple-Sclerosis—Distribution of T-Cell Subsets Within Active Chronic Lesions. Science 1983; 219: 308-310.

Trojano M, Paolicelli D, Bellacosa A, Cataldo S. The transition from relapsing-remitting MS to irreversible disability: clinical evaluation. Neurological Sciences 2003; 24: S268-S270.

Tsukamoto T, Seki H, Takase S, Sekizawa T, Nakamura S. Significant Increase in Immunosuppressive Acidic Protein (Iap) in Serum of Patients with Multiple-Sclerosis and Other Inflammatory Neurological Disorders. Journal of the Neurological Sciences 1986; 75: 353-361.

Tsunoda I, Kuang L Q, Theil D J, Fujinami R S. Antibody association with a novel model for primary progressive multiple sclerosis: induction of relapsing-remitting and progressive forms of EAE in H2s mouse strains. Brain Pathol. 2000; 10: 402-418.

van der Goes A, Boorsma W, Hoekstra K, Montagne L, de Groot C J A, Dijkstra C D. Determination of the sequential degradation of myelin proteins by macrophages. Journal of Neuroimmunology 2005; 161: 12-20.

Velasco E, Valero C, Valero A et al. Molecular analysis of the SMN and NAIP genes in Spanish spinal muscular atrophy (SMA) families and correlation between number of copies of (c)BCD541 and SNA phenotype (vol 5, pg 257, 1996). Human Molecular Genetics. 1996; 5:710.

Vischioni B, van der Valk P, Ing S W S, Kruyt F A E, Rodriguez J A, Giaccone G. Expression and localization of inhibitor of apoptosis proteins in normal human tissues. Human Pathology 2006; 37: 78-86.

Vizler C, Bercovici N, Cornet A, Cambouris C, Libau R S. Role of autoreactive CD8(+) T cells in organ-specific autoimmune diseases: insight from transgenic mouse models. Immunological Reviews 1999; 169: 81-92.

Zang Y C Q, Kozovska M M, Hong J et al. Impaired apoptotic deletion of myelin basic protein-reactive T cells in patients with multiple sclerosis. European Journal of Immunology 1999; 29: 1692-1700.

Zehntner, S. P., Bourbonntiere L., Morris S. J., Methot D., Doucet G., Durkin J., and Owens T. Damiano J S, Newman R M, Reed J C. Multiple roles of CLAN (caspase-associated recruitment domain, leucine-rich repeat, TPI-containing protein) in the and NAIP CIIA HET-E, and mammalian innate immune response. Journal of Immunology. 2004; 173:6338-6345.

Zehntner S P, Brickman C, Bourbonniere L, Remington L, Caruso M, Owens T. Neutrophils that infiltrate the central nervous system regulate T cell responses. J. Immunol. 2005b; 174: 5124-5131.

Other Embodiments

From the foregoing description, it will be apparent to one of ordinary skill in the art that variations and modifications may be made to the invention described herein to adapt it to various usages and conditions. Such embodiments are also within the scope of the present invention.

All publications mentioned in this specification are hereby incorporated by reference.

We claim:

1. A method for identifying a patient suffering from active relapsing remitting multiple sclerosis, the method comprising: a) determining an amount of XIAP and HIAP-2 gene expression levels in peripheral blood mononuclear (PBMN) cells obtained from the patient; and b) comparing the amount of the XIAP and HIAP-2 gene expression levels in the PBMN cells with the XIAP and HIAP-2 gene expression levels of control subjects, an increase in the XIAP and HIAP-2 gene expression levels being an indication that the patient is suffering from active relapsing remitting multiple sclerosis.

2. A method for determining whether a patient suffering from active relapsing remitting multiple sclerosis is at risk of developing secondary progressive multiple sclerosis, the method comprising: a) determining an amount of XIAP and HIAP-2 gene expression levels in peripheral blood mononuclear (PBMN) cells obtained from the patient; and b) comparing the amount of the XIAP and HIAP-2 gene expression levels in the PBMN cells with the XIAP and HIAP-2 gene expression levels of control subjects, an increase in the XIAP and HIAP-2 gene expression levels being an indication that the patient is at risk of developing secondary progressive multiple sclerosis.

3. The method, according to claim 1, in which the control subjects are those having benign MS or are healthy normal subjects.

4. The method, according to claim 1, in which the increased XIAP and HIAP-2 gene expression levels are determined by measuring the levels of transcribed XIAP mRNA and transcribed HIAP-2 mRNA in the PBMN cells.

5. The method, according to claim 4, in which the level of the transcribed mRNA is measured using quantitative real time polymerase chain reaction (qRT-PCR).

6. The method, according to claim 1, in which the PBMN cells are isolated from a blood sample taken from the patient.

7. The method, according to claim 2, in which the control subjects are those having benign MS or are healthy normal subjects.

8. The method, according to claim 2, in which the increased XIAP and HIAP-2 gene expression levels are determined by measuring the levels of transcribed XIAP mRNA and transcribed HIAP-2 mRNA in the PBMN cells.

9. The method, according to claim 8, in which the level of the transcribed mRNA is measured using quantitative real time polymerase chain reaction (qRT-PCR).

10. The method, according to claim 2, in which the PBMN cells are isolated from a blood sample taken from the patient.

* * * * *

```
                              SEQUENCE LISTING

<160> NUMBER OF SEQ ID NOS: 15

<210> SEQ ID NO 1
<211> LENGTH: 27
<212> TYPE: DNA
<213> ORGANISM: Homo sapiens

<400> SEQUENCE: 1
ggtgataaag taaagtgctt tcactgt                                           27

<210> SEQ ID NO 2
<211> LENGTH: 28
<212> TYPE: DNA
<213> ORGANISM: Homo sapiens

<400> SEQUENCE: 2
tcagtagttc ttaccagaca ctcctcaa                                          28

<210> SEQ ID NO 3
<211> LENGTH: 34
<212> TYPE: DNA
<213> ORGANISM: Homo sapiens
<220> FEATURE:
<221> NAME/KEY: misc_feature
<223> OTHER INFORMATION: FAM at 5'; TAMRA at 3'

<400> SEQUENCE: 3
caacatgcta aatggtatcc agggtgcaaa tatc                                   34

<210> SEQ ID NO 4
<211> LENGTH: 21
<212> TYPE: DNA
<213> ORGANISM: Homo sapiens

<400> SEQUENCE: 4
tggagatgat ccatgggttc a                                                 21

<210> SEQ ID NO 5
<211> LENGTH: 29
<212> TYPE: DNA
<213> ORGANISM: Homo sapiens

<400> SEQUENCE: 5
gaactcctgt cctttaattc ttatcaagt                                         29
```

```
<210> SEQ ID NO 6
<211> LENGTH: 27
<212> TYPE: DNA
<213> ORGANISM: Homo sapiens
<220> FEATURE:
<221> NAME/KEY: misc_feature
<223> OTHER INFORMATION: FAM at 5' TAMRA at 3'

<400> SEQUENCE: 6
ctcacacctt ggaaaccact tggcatg                                       27

<210> SEQ ID NO 7
<211> LENGTH: 23
<212> TYPE: DNA
<213> ORGANISM: Homo sapiens

<400> SEQUENCE: 7
tctggagatg atccatgggt aga                                           23

<210> SEQ ID NO 8
<211> LENGTH: 22
<212> TYPE: DNA
<213> ORGANISM: Homo sapiens

<400> SEQUENCE: 8
tggcctttca ttcgtatcaa ga                                            22

<210> SEQ ID NO 9
<211> LENGTH: 27
<212> TYPE: DNA
<213> ORGANISM: Homo sapiens
<220> FEATURE:
<221> NAME/KEY: misc_feature
<223> OTHER INFORMATION: FAM at 5' TAMRA at 3'

<400> SEQUENCE: 9
ctcacacctt ggaaaccact tggcatg                                       27

<210> SEQ ID NO 10
<211> LENGTH: 24
<212> TYPE: DNA
<213> ORGANISM: Homo sapiens

<400> SEQUENCE: 10
gccattttat gtccaaggga tatc                                          24

<210> SEQ ID NO 11
<211> LENGTH: 23
<212> TYPE: DNA
<213> ORGANISM: Homo sapiens

<400> SEQUENCE: 11
cttcccaatt tcctaaacac tca                                           23

<210> SEQ ID NO 12
<211> LENGTH: 35
<212> TYPE: DNA
<213> ORGANISM: Homo sapiens
<220> FEATURE:
<221> NAME/KEY: misc_feature
<223> OTHER INFORMATION: FAM at 5' TAMRA at 3'

<400> SEQUENCE: 12
ctgtaccgtg tcctgtttac ctgtaaagac aaagc                              35
```

-continued

```
<210> SEQ ID NO 13
<211> LENGTH: 20
<212> TYPE: DNA
<213> ORGANISM: Homo sapiens

<400> SEQUENCE: 13
tctgcttcaa agagctggaa                                                    20

<210> SEQ ID NO 14
<211> LENGTH: 18
<212> TYPE: DNA
<213> ORGANISM: Homo sapiens

<400> SEQUENCE: 14
gaaaggaaag cgcaaccg                                                      18

<210> SEQ ID NO 15
<211> LENGTH: 30
<212> TYPE: DNA
<213> ORGANISM: Homo sapiens
<220> FEATURE:
<221> NAME/KEY: misc_feature
<223> OTHER INFORMATION: FAM at 5' TAMRA at 3'

<400> SEQUENCE: 15
agccagatga cgaccccata gaggaacata                                         30
```